(12) United States Patent
Saito

(10) Patent No.: US 11,147,811 B2
(45) Date of Patent: Oct. 19, 2021

(54) COMPOSITION COMPRISING FINE PARTICLE AND PROCESS THEREOF

(71) Applicant: Sumitomo Dainippon Pharma Co., Ltd., Osaka (JP)

(72) Inventor: Shunsuke Saito, Ibaraki (JP)

(73) Assignee: Sumitomo Dainippon Pharma Co., Ltd., Osaka (JP)

(*) Notice: Subject to any disclaimer, the term of this patent is extended or adjusted under 35 U.S.C. 154(b) by 1 day.

(21) Appl. No.: 16/083,392

(22) PCT Filed: Mar. 9, 2017

(86) PCT No.: PCT/JP2017/009428
§ 371 (c)(1),
(2) Date: Sep. 7, 2018

(87) PCT Pub. No.: WO2017/155020
PCT Pub. Date: Sep. 14, 2017

(65) Prior Publication Data
US 2019/0083490 A1    Mar. 21, 2019

(30) Foreign Application Priority Data

Mar. 10, 2016    (JP) .............................. JP2016-047607

(51) Int. Cl.
*A61K 9/10*      (2006.01)
*A61K 31/499*    (2006.01)
(Continued)

(52) U.S. Cl.
CPC .............. *A61K 31/499* (2013.01); *A61K 9/10* (2013.01); *A61K 9/16* (2013.01); *A61K 9/1623* (2013.01);
(Continued)

(58) Field of Classification Search
CPC ....................................................... A61K 9/10
See application file for complete search history.

(56) References Cited

U.S. PATENT DOCUMENTS 5,885,491 A * 3/1999 Galan Valdivia .... A61K 9/5153
264/4.1
6,297,244 B1   10/2001 Ohashi et al.
(Continued)

FOREIGN PATENT DOCUMENTS

CN    102256597 A    11/2011
EP    2 623 100 A1    8/2013
(Continued)

OTHER PUBLICATIONS

Yammine et al (Journal of Advances in Chemistry, vol. 11, No. 4 (2015) 3454-3464). (Year: 2015).*
Elchidana et al (Journal of Controlled Release 59 (1999) 279-285). (Year: 1999).*
International Search Report dated Apr. 11, 2017 in PCT/JP2017/009428, 2 pages.
(Continued)

*Primary Examiner* — Benjamin J Packard
(74) *Attorney, Agent, or Firm* — Oblon, McClelland, Maier & Neustadt, L.L.P.

(57) ABSTRACT

The present invention relates to a comprising (A) an active ingredient which is hardly soluble in water, but soluble in a $C_{1-4}$ lower alcohol that may contain 30 vol % or less water, (B) polyvinyl alcohol having a saponification rate of 55-99%, and (C) a non-ionic surfactant, wherein the (A) active ingredient has a mean particle size of 10-300 nm, and a process thereof.

38 Claims, 21 Drawing Sheets

(51) Int. Cl.
  A61K 47/10   (2017.01)
  A61K 47/14   (2017.01)
  A61K 47/32   (2006.01)
  A61K 47/34   (2017.01)
  A61K 9/19    (2006.01)
  A61K 31/405  (2006.01)
  A61K 31/496  (2006.01)
  A61K 9/16    (2006.01)
  A61K 47/26   (2006.01)

(52) U.S. Cl.
  CPC .......... *A61K 9/1635* (2013.01); *A61K 9/1641* (2013.01); *A61K 9/19* (2013.01); *A61K 31/405* (2013.01); *A61K 31/496* (2013.01); *A61K 47/10* (2013.01); *A61K 47/14* (2013.01); *A61K 47/26* (2013.01); *A61K 47/32* (2013.01); *A61K 47/34* (2013.01)

(56) References Cited

U.S. PATENT DOCUMENTS

| | | | |
|---|---|---|---|
| 2011/0237686 A1 | 9/2011 | Ng et al. | |
| 2012/0022169 A1* | 1/2012 | Moriuchi | A61K 9/4866 514/772.4 |
| 2013/0122058 A1 | 5/2013 | Chow et al. | |
| 2013/0203723 A1 | 8/2013 | Sakuma et al. | |
| 2013/0209521 A1 | 8/2013 | Filipcsei et al. | |
| 2013/0337077 A1 | 12/2013 | Wong et al. | |
| 2014/0212501 A1 | 7/2014 | Giardiello et al. | |
| 2014/0328919 A1 | 11/2014 | Zhang et al. | |
| 2015/0087624 A1 | 3/2015 | Baba et al. | |
| 2015/0250728 A1 | 9/2015 | Murata et al. | |
| 2016/0128944 A1 | 5/2016 | Chawrai et al. | |
| 2016/0361293 A1 | 12/2016 | Filipcsei et al. | |

FOREIGN PATENT DOCUMENTS

| | | |
|---|---|---|
| JP | 2004-175752 A | 6/2004 |
| JP | 2005-213170 A | 8/2005 |
| JP | 2005-298347 A | 10/2005 |
| JP | 2013-528642 A | 7/2013 |
| KR | 10-2016-0015335 A | 2/2016 |
| WO | WO 99/20276 A1 | 4/1999 |
| WO | WO 2005/072707 A1 | 8/2005 |
| WO | WO 2012/169518 A1 | 12/2012 |
| WO | WO 2013/034926 A1 | 3/2013 |
| WO | WO 2013/161778 A1 | 10/2013 |
| WO | WO 2014/050910 A1 | 4/2014 |
| WO | WO 2015/128685 A1 | 9/2015 |

OTHER PUBLICATIONS

English translation of International Preliminary Report on Patentability and Written Opinion of the International Searching Authority dated Sep. 20, 2018 in PCT/JP2017/009428 filed Mar. 9, 2017, 14 pages.

Yoshiaki Kawashima, "Functional Expression of Pharmaceutical Nanoparticulates by Composition" Journal of the Society of Powder Technology, Japan, vol. 41, No. 6, 2004, pp. 418-423.

Ayao Kitahara, et al., "Chemistry of Dispersal and Emulsified System", 3rd edition, Kogaku Tosho Kabushiki Kaisha, Co. Ltd., 1983, pp. 56-61.

Kuraray Poval, Grade List archive of a web page "http://www.poval.jp/japan/poval/gradelist/gl_04.html" archived in a web page "WayBackMachine", Nov. 7, 2012, 2 pages.

Masaru Oya, "Illustrated Introduction to Basics and Structure of the Latest Washing and Detergent: Basic Knowledge of Aqueous/Nonaqueous Cleaning and Mechanical Cleaning: Mechanism of Stain Removal" Shuwa System Co., Ltd., 2011, pp. 142 to 143 and cover pages.

Tetsuo Nakazawa, et al., "Study on the Self-Hardening Mold Bonded by Polyvinyl Alcohol" IMONO, vol. 55, No. 5, 1983, pp. 285 to 290.

Extended European Search Report dated Oct. 14, 2019 in European Patent Application No. 17763360.9, 13 pages.

Fonte, P., et al., "Facts and evidences on the lyophilization of polymeric nanoparticles for drug delivery", Journal of Controlled Release, vol. 225, 2016, XP029438890, pp. 75-86.

D'Addio, S.M., et al., "Controlling drug nanoparticle formation by rapid precipitation", Advanced Drug Delivery Reviews, vol. 63 No. 6, 2011, XP028374101, pp. 417-426.

Verma, S., et al., "Physical stability of nanosuspensions: Investigation of the role of stabilizers on Ostwald ripening", International Journal of Pharmaceutics vol. 406 No. 1, 2011, XP028363293, pp. 145-152.

"Development and study of new pharmaceuticals", CPCH1862444P, ISBN 978-7-5067-3929-0, Dec. 2008 (with Partial English Translation).

Hwang et al., "Production and dispersion stability of nanoparticles in nanofluids", Powder Technology, 186, (2008), pp. 145-153.

Xia et al., "Preparation of stable nitrendipine nanosuspensions using the precipitation-ultrasonication method for enhancement of dissolution and oral bioavailability", European Journal of Pharmaceutical Sciences, 2010, vol. 40, No. 4, pp. 325-334.

Thorat et al., "Liquid antisolvent precipitation and stabilization of nanoparticles of poorly water soluble drugs in aqueous suspensions: Recent developments and future perspective", Chemical Engineering Journal, 2012, vol. 181-182, pp. 1-34.

* cited by examiner

COMPOSITION COMPRISING FINE PARTICLE AND PROCESS THEREOF

TECHNICAL FIELD

The present invention relates to a suspension or solid composition comprising a fine particle of an active ingredient, and a process thereof.

BACKGROUND ART

As a method to prepare a fine solid active ingredient, breakdown method, i.e., a method of micronizing a solid active ingredient having a certain particle size with a physical action such as milling is the mainstream. However, it is known that the micronization needs high energy, and there is a limitation in the particle size micrified by breakdown method, said limitation of the mean particle size is about 200-300 nm. In addition, some active ingredients can take a very long time to be micronized, which depends on their physical property, and it is difficult to perfectly control the heat generated in micronization. Thus, it is not so easy from the industrial viewpoint to prepare nano-sized fine particles by breakdown method.

As an alternative method of preparing a nano-sized fine particle, build-up method has been known, in which an ingredient dissolved in a solvent is assembled each other or grown-up to obtain a fine particle thereof. As a nano-sized particle prepared by build-up method, a molecular assembly such as liposome, a polymer fine particle prepared by depositing a polymer as matrix, and the like have been studied (Patent Literature 1). However, these matrix-type fine particles are just a low molecular active ingredient supported in a fine particle additive, that is, it is not a method to prepare a nano-sized fine particle consisting of a low molecular active ingredient itself.

As ways to prepare a fine particle of a low molecular active ingredient by build-up method, a way has been known to make a crystallization by mixing a solution of an active ingredient (good solvent) and a solvent having a poor solubility to the active ingredient (poor solvent) (Patent Literatures 2 and 3). However, these ways require some specific excipients or a special manufacturing equipment, which were difficult to be generally applied. In order to prepare a very fine nano-sized particle by a crystallization, it is necessary to increase the mixing ratio of a poor solvent in a crystallization step, but thereby it is a problem that the concentration of the active ingredient in a finally-prepared suspension (the production amount of particles per unit volume) is low.

If the suspension comprising a nano-sized active ingredient is made to be a solid state by lyophilization or the like to be temporarily stored and then it is re-suspended before use, it is expected that the utility is enhanced to be available on various uses. Until now, however, there had not been any known methods to prepare a solid composition in which a nano-sized particle of an active ingredient having a mean particle size of 300 nm or lower can be stably re-produced after re-suspending.

PRIOR ART

Patent Reference

[Patent Literature 1] JP 2005-213170 A
[Patent Literature 2] WO 2013/161778
[Patent Literature 3] JP 2013-528642 A
[Patent Literature 4] WO 1999/20276

SUMMARY OF INVENTION

Technical Problem

As mentioned above, it has been desired to develop a novel build-up method to prepare a fine particle of an active ingredient having a mean particle size of nano order such as 10-300 nm in high concentration, a novel solid composition available for various uses in which a nano-sized particle of an active ingredient having a mean particle size of nano order can be stably maintained, and a novel process thereof.

Solution to Problem

The present inventors have extensively studied to reach the above object, and then have found that a suspension composition comprising a fine particle of an active ingredient in high concentration can be stably prepared by dissolving an active ingredient (which is hardly soluble in water) in $C_{1-4}$ organic solvent that may contain 30 vol % or less water, and mixing the obtained solution with water containing polyvinyl alcohol in the presence of a surfactant. In addition, the present inventors have found that a re-suspension composition prepared by drying the obtained suspension composition and then re-dispersing it in a dispersion media can be maintained in a fine particle without the crystal growth of the active ingredient. That is, the present invention has made it possible to stably prepare a suspension composition comprising a fine particle of an active ingredient in high concentration and a solid composition thereof. Based upon the new findings, the present invention has been completed.

The summary of the present invention can show as follows.

(Tem 1)
A composition comprising
(A) an active ingredient which is hardly soluble in water, but soluble in a $C_{1-4}$ lower alcohol that may contain 30 vol % or less water,
(B) polyvinyl alcohol having a saponification rate of 55-99%, and
(C) a non-ionic surfactant,
wherein the (A) active ingredient has a mean particle size of 10-300 nm.

(Term 2)
The composition of Term 1, wherein the D90 particle size of the (A) active ingredient is 300 nm or less.

(Term 3)
The composition of Term 1 or 2, wherein the mean particle size of the (A) active ingredient is 10-200 nm.

(Term 4)
The composition of any one of Terms 1-3, wherein the (A) active ingredient is (R)-(−)-2-(4-bromo-2-fluorobenzyl)-1,2,3,4-tetrahydropyrrolo[1,2-a]pyrazine-4-spiro-3'-pyrrolidine-1,2',3,5'-tetraone, 2-(4-ethyl-1-piperazinyl)-4-(4-fluorophenyl)-5,6,7,8,9,10-hexahydrocycloocta[b]pyridine, indomethacin, or a pharmaceutically acceptable salt thereof.

(Term 5)
The composition of any one of Terms 1-4, wherein the molecular weight of the (B) polyvinyl alcohol is 150000 or less.

(Term 6)
The composition of any one of Terms 1-5, wherein the content of the (B) polyvinyl alcohol is 0.5 to 5 parts by weight per 1 part by weight of the (A) active ingredient.

(Term 7)

The composition of any one of Terms 1-6, wherein the (C) non-ionic surfactant is one or more selected from the group consisting of polyoxyethylene polyoxypropylene glycol, polyoxyethylene hydrogenated castor oil, polyoxyethylene castor oil, polyoxyethylene sorbitan fatty acid ester, polyethylene glycol monostearate, sorbitan monooleate, sorbitan sesquioleate, glyceryl monooleate, and polyvinyl alcohol having a saponification rate of less than 55%.

(Term 8)

The composition of Term 7, wherein the (C) non-ionic surfactant is polyoxyethylene polyoxypropylene glycol comprising one or more kinds of polyoxyethylene units in 40 wt % or more.

(Term 9)

The composition of Term 8, wherein the polyoxyethylene polyoxypropylene glycol is one or more selected from polyoxyethylene (160) polyoxypropylene (30) glycol, and polyoxyethylene (200) polyoxypropylene (70) glycol.

(Term 10)

The composition of any one of Terms 1-9, wherein the content of the (C) non-ionic surfactant is 0.02 to 0.8 parts by weight per 1 part of the (A) active ingredient.

(Term 11)

The composition of Term 10, wherein the content of the (C) non-ionic surfactant is 0.02 to 0.45 parts by weight per 1 part of the (A) active ingredient.

(Term 12)

The composition of Term 11, wherein the content of the (C) non-ionic surfactant is 0.02 to 0.2 parts by weight per 1 part of the (A) active ingredient.

(Term 13)

The composition of any one of Terms 1-12, further comprising poly(2-methacryloyloxy phosphorylcholine)-poly(n-butyl methacrylate).

(Term 14)

The composition of Term 13, wherein the content of the poly(2-methacryloyloxy phosphorylcholine)-poly(n-butyl methacrylate) is 0.05 to 0.6 parts by weight per 1 part of the (A) active ingredient.

(Term 15)

The composition of any one of Terms 1-14, further comprising a pharmaceutically acceptable excipient.

(Term 16)

The composition of Term 15, wherein the excipient is one or more selected from the group consisting of mannitol, trehalose, and lactose.

(Term 17)

The composition of any one of Terms 1-16, which is characterized in that the (A) active ingredient can be kept in a suspension state when the composition is dispersed in an aqueous dispersion media.

(Term 18)

The composition of Term 17, wherein the aqueous dispersion media is water.

(Term 19)

The composition of any one of Terms 1-18, wherein the composition is a solid composition.

(Term 20)

The composition of any one of Terms 1-19, further comprising an aqueous dispersion media.

(Term 21)

The composition of Term 20, wherein the aqueous dispersion media is water.

(Term 22)

The composition of any one of Terms 1-18, further comprising (D) a mixed solution comprising $C_{1-4}$ lower alcohol and water whose water content is 50 vol % or more, wherein the (A) active ingredient in the (D) mixed solution is a manufacturing intermediate which is kept in a suspension state.

(Term 23)

The composition of Term 22, wherein the composition is a suspension composition.

(Term 24)

The composition of Term 22 or 23, wherein the water content of the (D) mixed solution is 65 vol % or more.

(Term 25)

The composition of any one of Terms 22-24, wherein the lower alcohol in the (D) mixed solution is one or more selected from the group consisting of ethanol, 1-propanol, 2-propanol, 1,1-dimethylethanol, 1,2-ethanediol, 1,2-propanediol, 1,3-propanediol, and 1,2,3-propanetriol.

(Term 26)

The composition of Term 25, wherein the lower alcohol in the (D) mixed solution is ethanol or 1,1-dimethylethanol.

(Term 27)

The composition of Term 26, wherein the lower alcohol in the (D) mixed solution is 1,1-dimethylethanol.

(Term 28)

The composition of any one of Terms 22-27, wherein the content of the (A) active ingredient is 1.5-20 mg/mL.

(Term 29)

The composition of any one of Terms 22-28, which is filter-sterilizable.

(Term 30)

The composition of any one of Terms 1-19, which is a solid composition obtained by drying the composition of any one of Terms 22-29.

(Term 31)

A process to prepare the composition of any one of Terms 1-30, comprising the following step:

mixing Liquid 1 comprising the (A) active ingredient in a water-miscible $C_{1-4}$ organic solvent that may contain 30 vol % or less water, and Liquid 2 comprising the (B) polyvinyl alcohol having a saponification rate of 55-99%, wherein Liquid 1 and/or Liquid 2 comprise the (C) non-ionic surfactant.

(Term 32)

The process of Term 31, wherein Liquid 1 comprises the (C) non-ionic surfactant.

(Term 33)

The process of Term 31 or 32, wherein the volume ratio of Liquid 1 and Liquid 2 to be mixed is 0.5:9.5-4:6.

(Term 34)

The process of Term 33, wherein the volume ratio of Liquid 1 and Liquid 2 to be mixed is 0.5:9.5-3.5:6.5.

(Term 35)

The process of any one of Terms 31-34, wherein the content of the (A) active ingredient in the total of Liquid 1 and Liquid 2 is 1.5-20 mg/mL.

(Term 36)

The process of any one of Terms 31-35, wherein the water-miscible $C_{1-4}$ organic solvent is one or more selected from the group consisting of a $C_{1-4}$ lower alcohol and acetone.

(Term 37)

The process of any one of Terms 31-36, wherein the water-miscible $C_{1-4}$ organic solvent is a $C_{1-4}$ lower alcohol.

(Term 38)

The process of Term 36 or 37, wherein the $C_{1-4}$ lower alcohol is one or more selected from the group consisting of ethanol, 1-propanol, 2-propanol, 1,1-dimethylethanol, 1,2-ethanediol, 1,2-propanediol, 1,3-propanediol, and 1,2,3-propanetriol.
(Term 39)
The process of Term 38, wherein the lower alcohol is ethanol or 1,1-dimethylethanol.
(Term 40)
The process of Term 39, wherein the lower alcohol is 1,1-dimethylethanol.
(Term 41)
The process of any one of Terms 31-40, wherein the molecular weight of the (B) polyvinyl alcohol is 150000 or less.
(Term 42)
The process of any one of Terms 31-41, wherein the content of the (B) polyvinyl alcohol is 0.5 to 5 parts by weight per 1 part by weight of the (A) active ingredient.
(Term 43)
The process of any one of Terms 31-42, wherein the (C) non-ionic surfactant is one or more selected from the group consisting of polyoxyethylene polyoxypropylene glycol, polyoxyethylene hydrogenated castor oil, polyoxyethylene castor oil, polyoxyethylene sorbitan fatty acid ester, polyethylene glycol monostearate, sorbitan monooleate, sorbitan sesquioleate, glyceryl monooleate, and polyvinyl alcohol having a saponification rate of less than 55%.
(Term 44)
The process of Term 43, wherein the (C) non-ionic surfactant is polyoxyethylene polyoxypropylene glycol comprising one or more kinds of polyoxyethylene units in 40 wt % or more.
(Term 45)
The process of Term 44, wherein the polyoxyethylene polyoxypropylene glycol is one or more selected from polyoxyethylene (160) polyoxypropylene (30) glycol, and polyoxyethylene (200) polyoxypropylene (70) glycol.
(Term 46)
The process of any one of Terms 31-45, wherein the content of the (C) non-ionic surfactant is 0.02 to 0.8 parts by weight per 1 part of the (A) active ingredient.
(Term 47)
The process of any one of Terms 31-46, wherein Liquid 1 comprises the (C) non-ionic surfactant, and Liquid 2 further comprises poly(2-methacryloyloxy phosphorylcholine)-poly(n-butyl methacrylate).
(Term 48)
The process of Term 47, wherein the content of the poly(2-methacryloyloxy phosphorylcholine)-poly(n-butyl methacrylate) is 0.05 to 0.6 parts by weight per 1 part of the (A) active ingredient.
(Term 49)
The process of any one of Terms 31-48, wherein Liquid 1 comprises the (C) non-ionic surfactant, and Liquid 2 further comprises a pharmaceutically acceptable excipient.
(Term 50)
The process of any one of Terms 31-49, which further comprises a step of filter-sterilizing the mixture of Liquid 1 and Liquid 2.
(Term 51)
The process of any one of Terms 31-50, wherein the (A) active ingredient is (R)-(−)-2-(4-bromo-2-fluorobenzyl)-1,2,3,4-tetrahydropyrrolo[1,2-a]pyrazine-4-spiro-3'-pyrrolidine-1,2',3,5'-tetraone, 2-(4-ethyl-1-piperazinyl)-4-(4-fluorophenyl)-5,6,7,8,9,10-hexahydrocycloocta[b]pyridine, indomethacin, or a pharmaceutically acceptable salt thereof.

(Term 52)
A process to prepare a solid composition by drying in vacuo the suspension composition prepared in any one of Terms 31-51.
(Term 53)
A process to a suspension, comprising by suspending the solid composition prepared in Term 52 in an aqueous dispersion media.
(Term 54)
The process of Term 53, wherein the aqueous dispersion media is water.
(Term 55)
The composition of any one of Terms 1-19, which is prepared by the process of Term 52.
(Term 56)
A composition comprising the composition of Term 55 and an aqueous dispersion media.
(Term 57)
A process to prepare a suspension composition comprising the (A) active ingredient which is hardly soluble in water, but soluble in a water-miscible $C_{1-4}$ organic solvent that may contain 30 vol % or less water, wherein the (A) active ingredient has a mean particle size of 10-1000 nm, comprising the following step:
mixing Liquid 1 comprising the (A) active ingredient in a water-miscible $C_{1-4}$ organic solvent that may contain 30 vol % or less water, and Liquid 2 comprising the (B) polyvinyl alcohol having a saponification rate of 55-99%,
wherein Liquid 1 and/or Liquid 2 comprise the (C) non-ionic surfactant.
(Term 58)
The process of Term 57, wherein the mean particle size of the (A) active ingredient in the composition is 10-600 nm.
(Term 59)
The process of Term 57, wherein the mean particle size of the (A) active ingredient in the composition is 10-400 nm.
(Term 60)
The process of Term 57, wherein the mean particle size of the (A) active ingredient in the composition is 10-200 nm.
Terms 57-60 may include the embodiments of the limitations in the processes of Term 31-term 54.

Effect of the Invention

The present invention can provide a suspension/solid composition comprising an active ingredient which is hardly soluble in water as a fine particle having a mean particle size of, for example, 10-300 nm (preferably, 10-200 nm). In general, an active ingredient which is hardly soluble in water has a low absorption into the body, but the present invention provides a formulation comprising an active ingredient whose mean particle size is 10-300 nm, which has a high absorption into the body. In addition, a formulation comprising an active ingredient whose mean particle size is 10-300 nm can be filter-sterilized, and it can be provided as a sterile formulation such as injection and eye drop. Furthermore, by getting an active ingredient to be a fine particle thereof whose mean particle size is 10-300 nm, a formulation comprising the active ingredient can be provided which has some functions such as sustained-release and targeting at pathology site. That is, the present invention can make an active ingredient which is hardly soluble in water applied to various administration routes and can provide a formulation comprising the active ingredient which has some high functions.

In addition, a solid composition which can keep an active ingredient therein as a fine particle whose mean particle size is 10-300 nm is useful as a solid formulation for preparing a liquid formulation comprising its fine particle before using and an oral solid formulation, and the technique can apply to any various active ingredients.

Furthermore, a suspension composition which is a manufacturing intermediate in the present invention comprises a high concentration of an active ingredient in a suspension, and thus it is possible to make operation with high volumetric efficiency in preparing a solid composition by lyophilization after producing the manufacturing intermediate.

DESCRIPTION OF EMBODIMENTS

Figure 1:
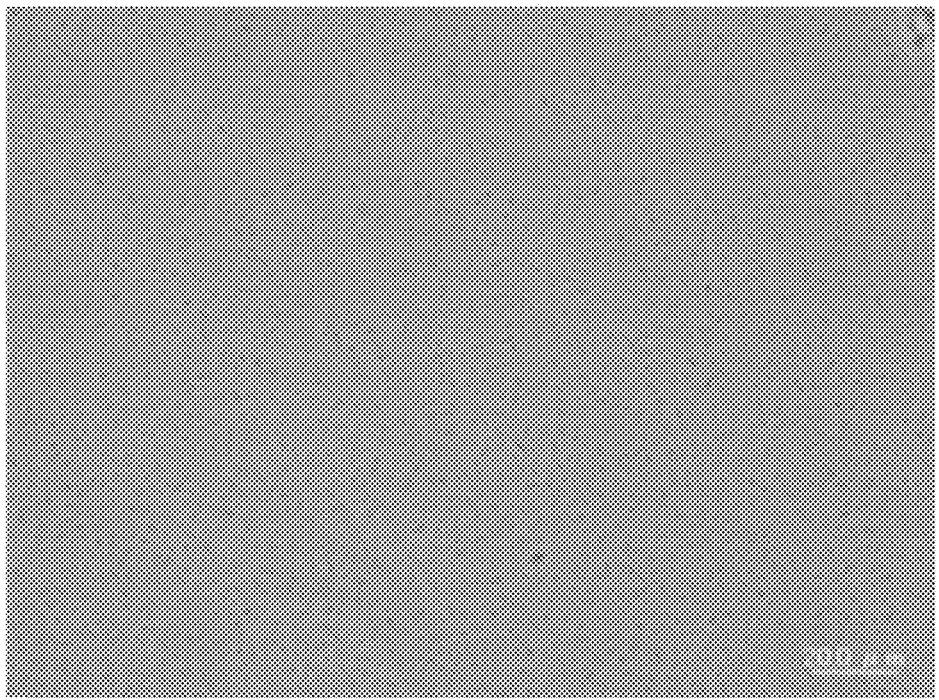
FIG. 1 shows an optical microscopic image of the suspension in Example 1 (×400).
Figure 2:
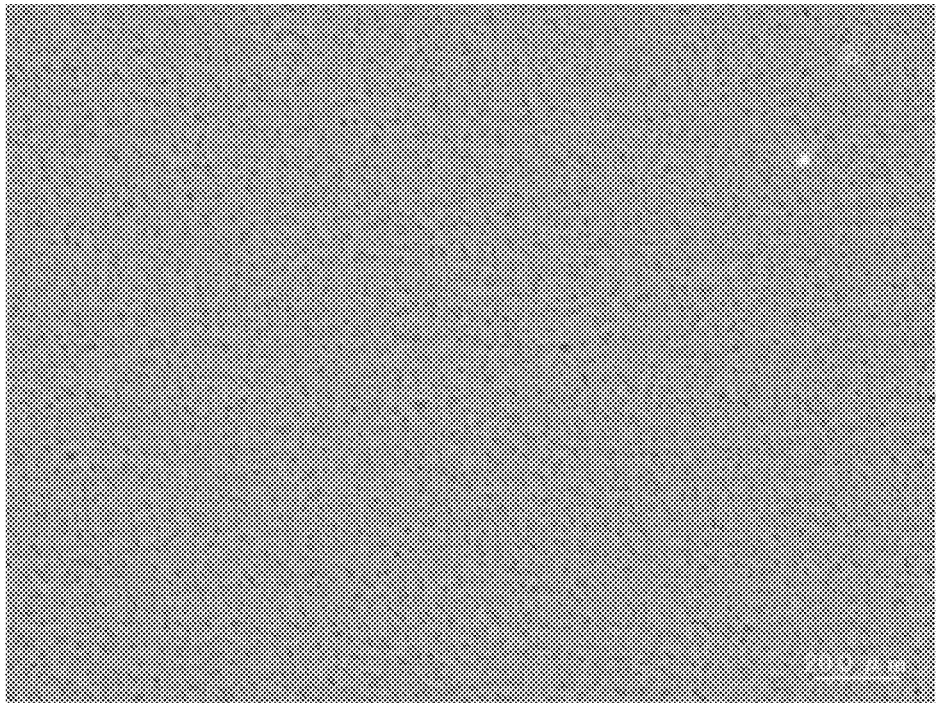
FIG. 2 shows an optical microscopic image of the suspension in Example 2 (×400).
Figure 3:
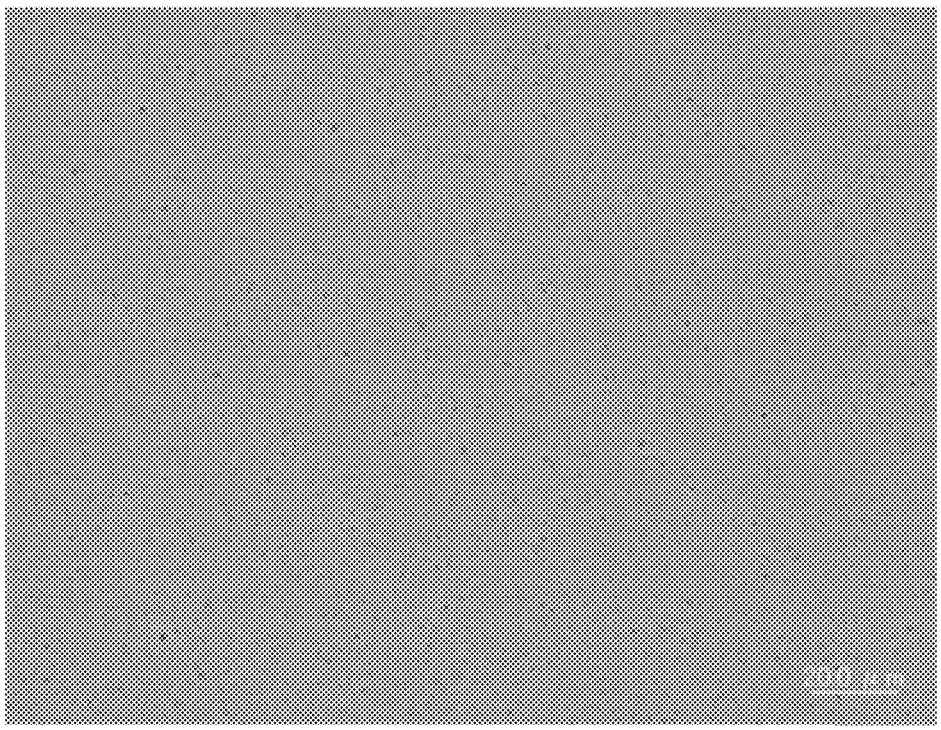
FIG. 3 shows an optical microscopic image of the suspension in Example 3 (×400).
Figure 4:
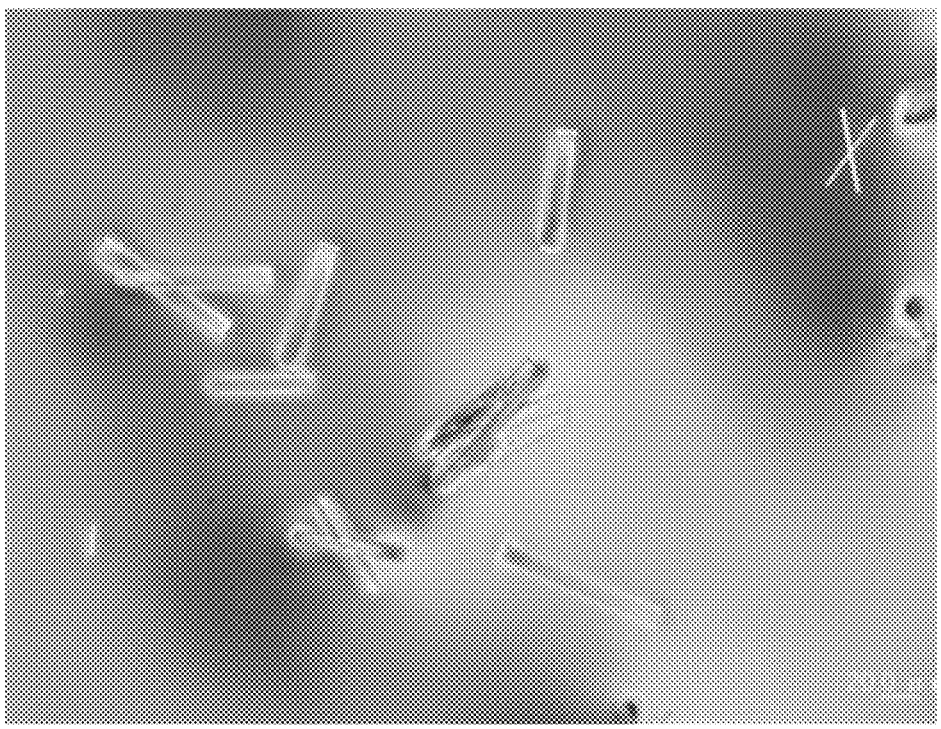
FIG. 4 shows an optical microscopic image of the suspension in Comparative example 1 (×200).
Figure 5:
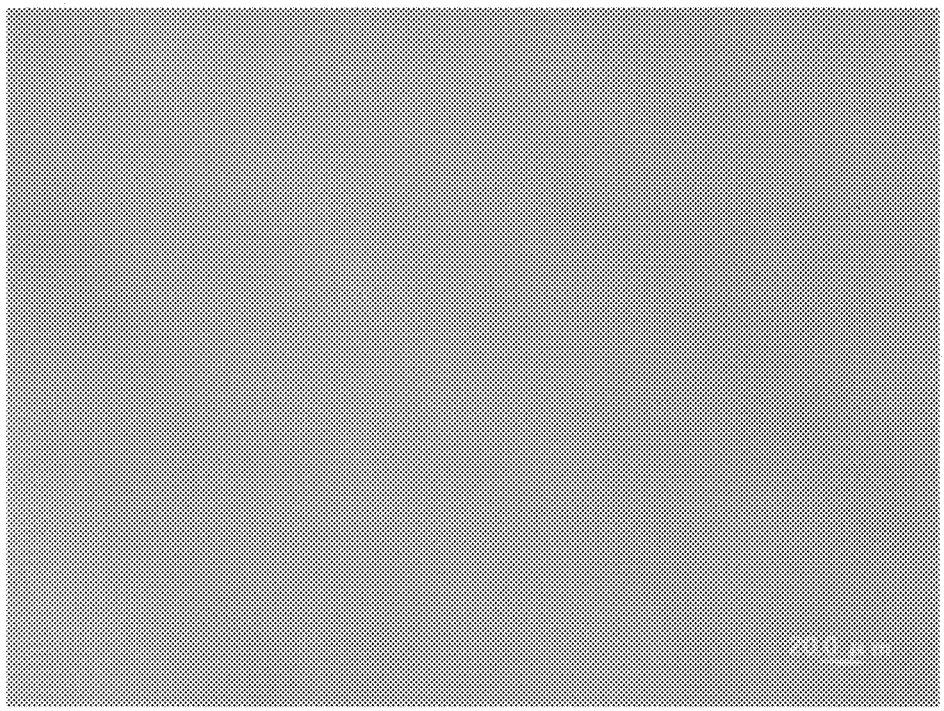
FIG. 5 shows an optical microscopic image of the suspension in Example 4 (×200).
Figure 6:
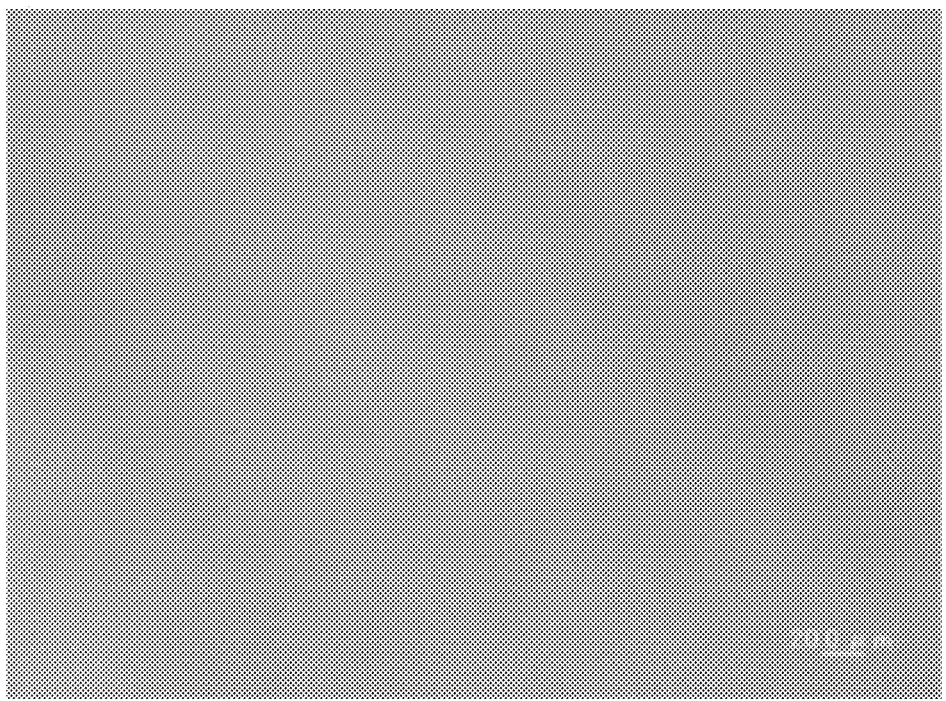
FIG. 6 shows an optical microscopic image of the suspension in Example 5 (×200).
Figure 7:
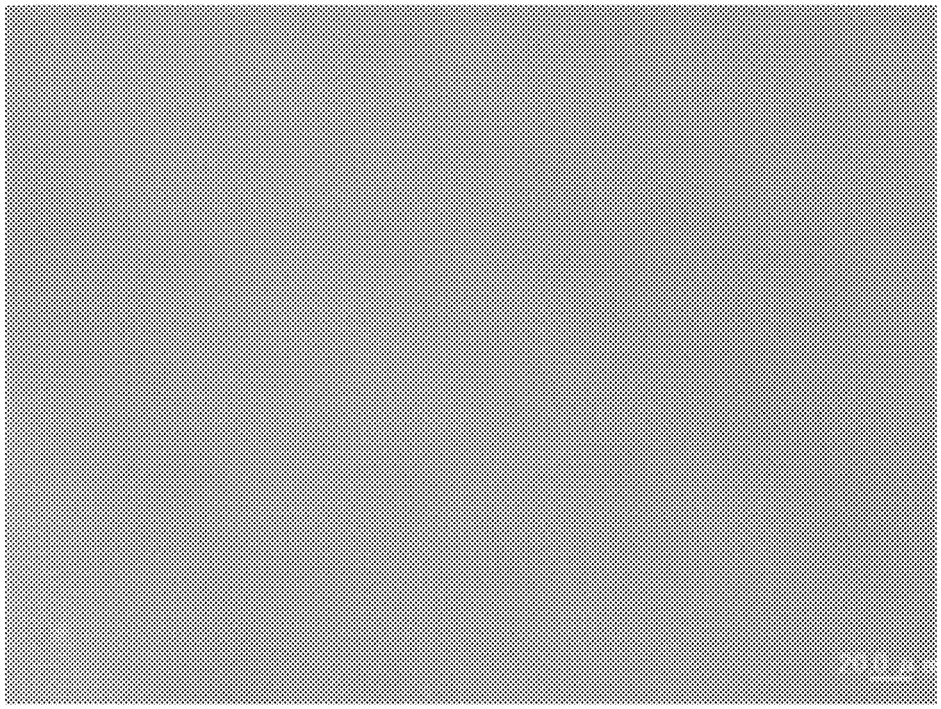
FIG. 7 shows an optical microscopic image of the suspension in Example 6 (×200).
Figure 8:
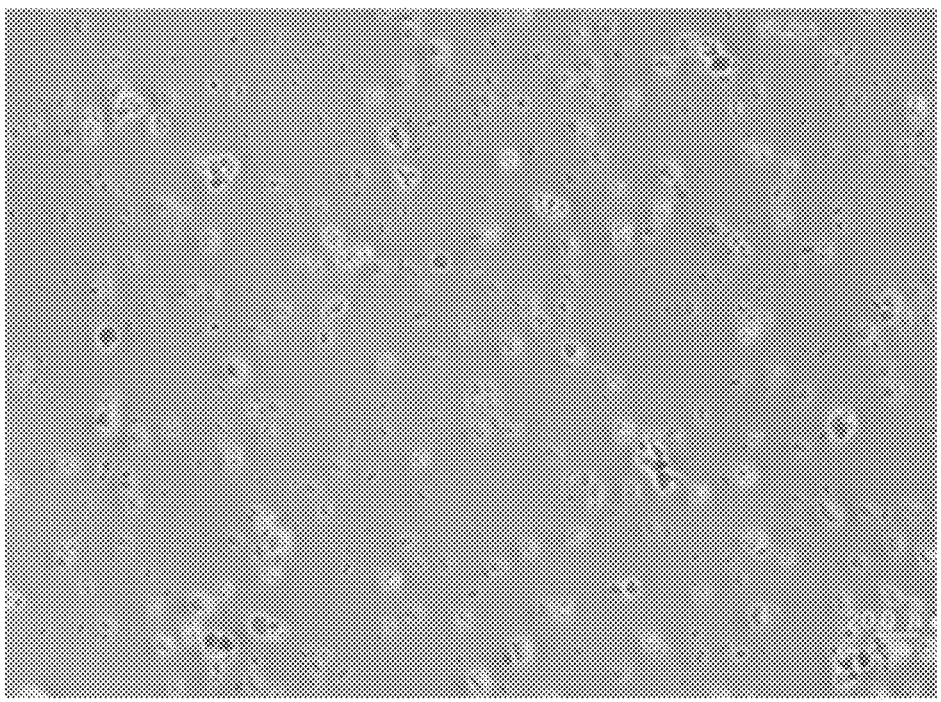
FIG. 8 shows an optical microscopic image of the suspension in Comparative example 2 (×200).
Figure 9:
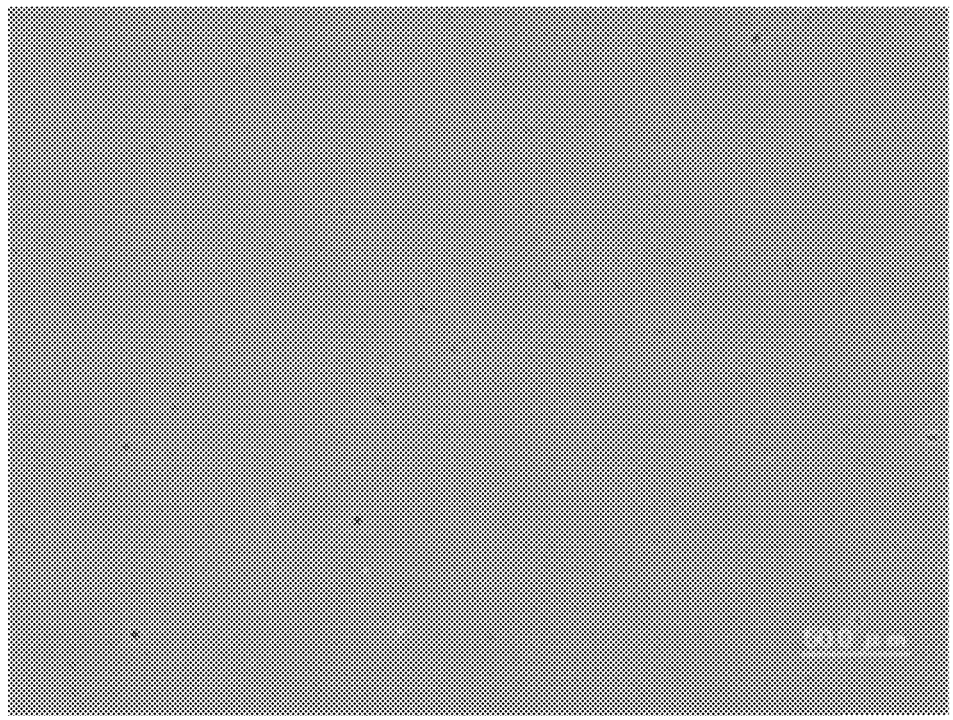
FIG. 9 shows an optical microscopic image of the pre-lyophilized suspension in Comparative example 3 (×400).
Figure 10:
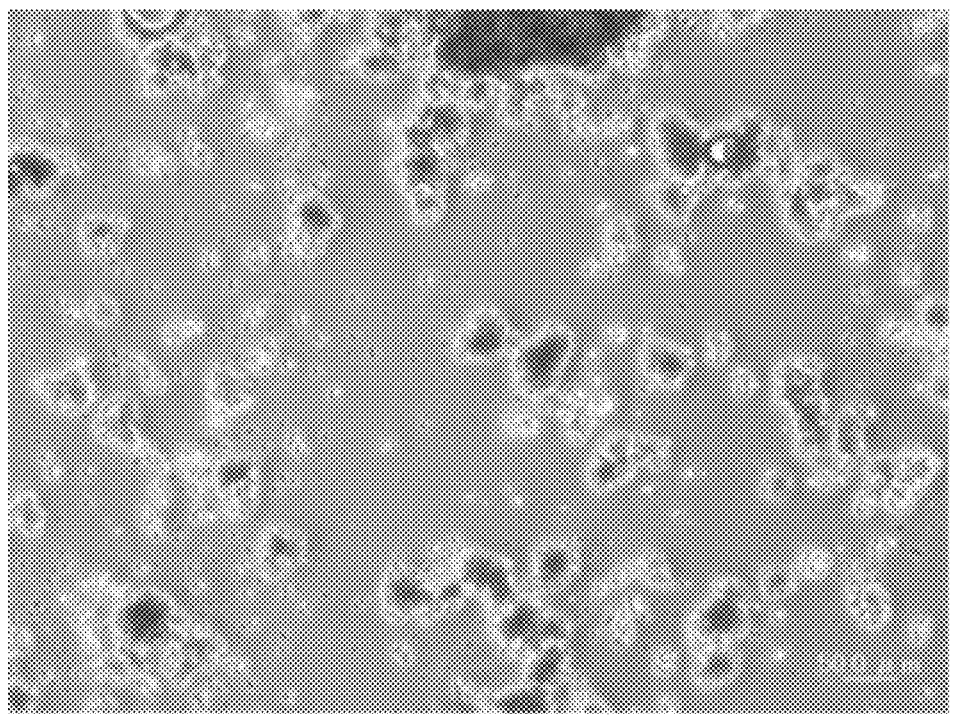
FIG. 10 shows an optical microscopic image of the suspension prepared by re-suspending the lyophilized product of Comparative example 3 in water (×200).
Figure 11:
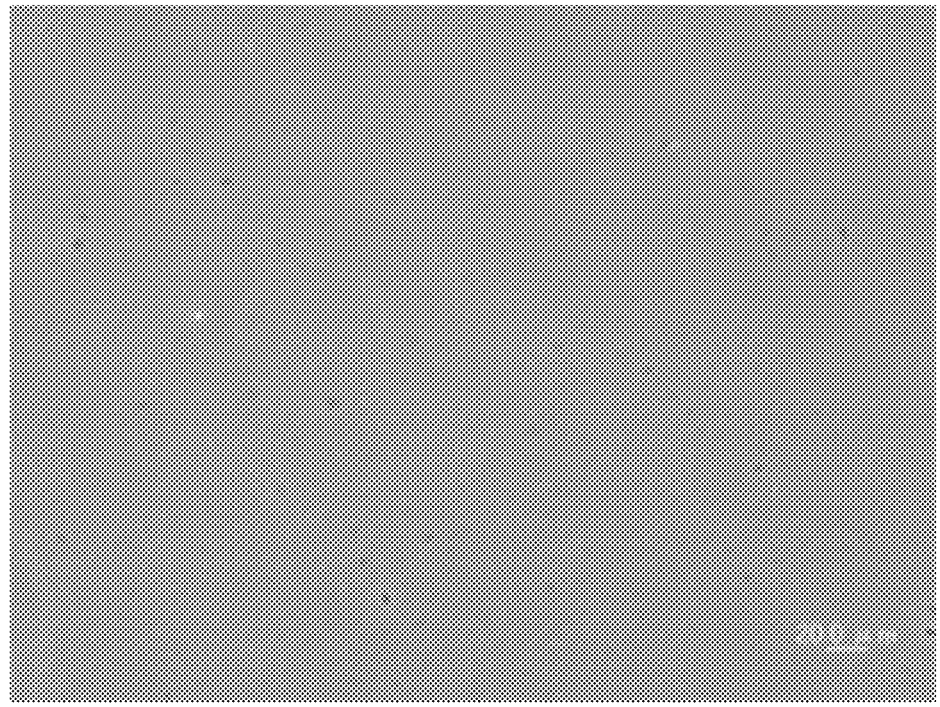
FIG. 11 shows an optical microscopic image of the pre-lyophilized suspension in Comparative example 4 (×400).
Figure 12:
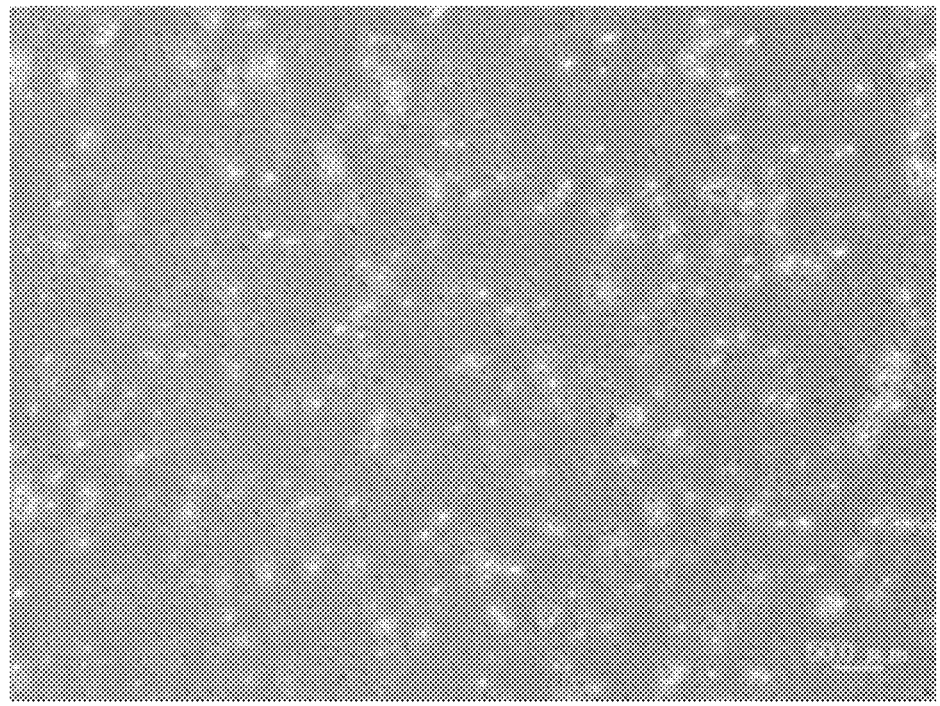
FIG. 12 shows an optical microscopic image of the suspension prepared by re-suspending the lyophilized product of Comparative example 4 in water (×200).
Figure 13:
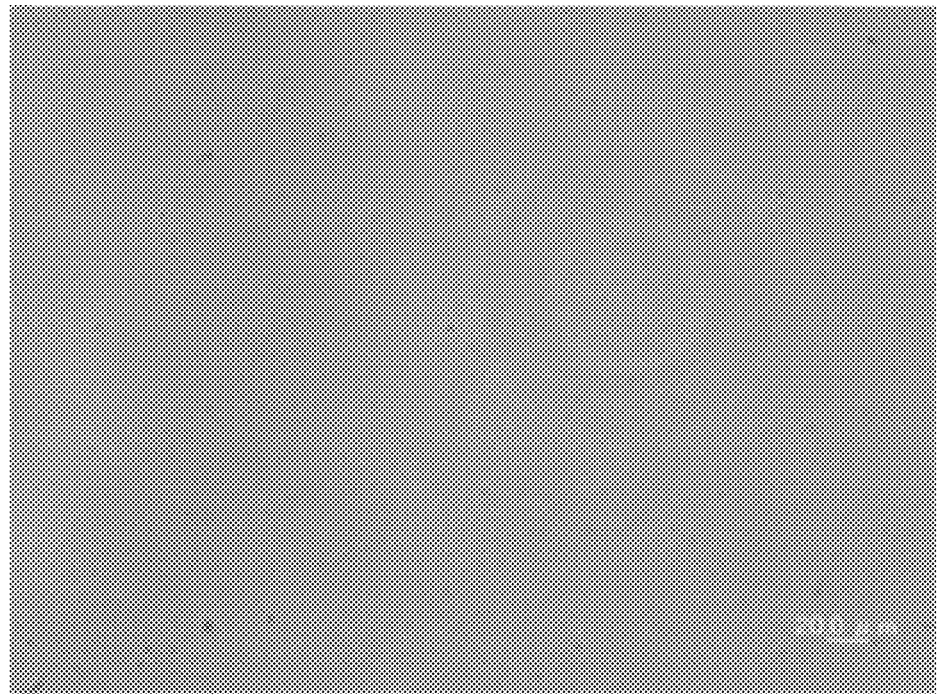
FIG. 13 shows an optical microscopic image of the pre-lyophilized suspension in Example 7 (×400).
Figure 14:
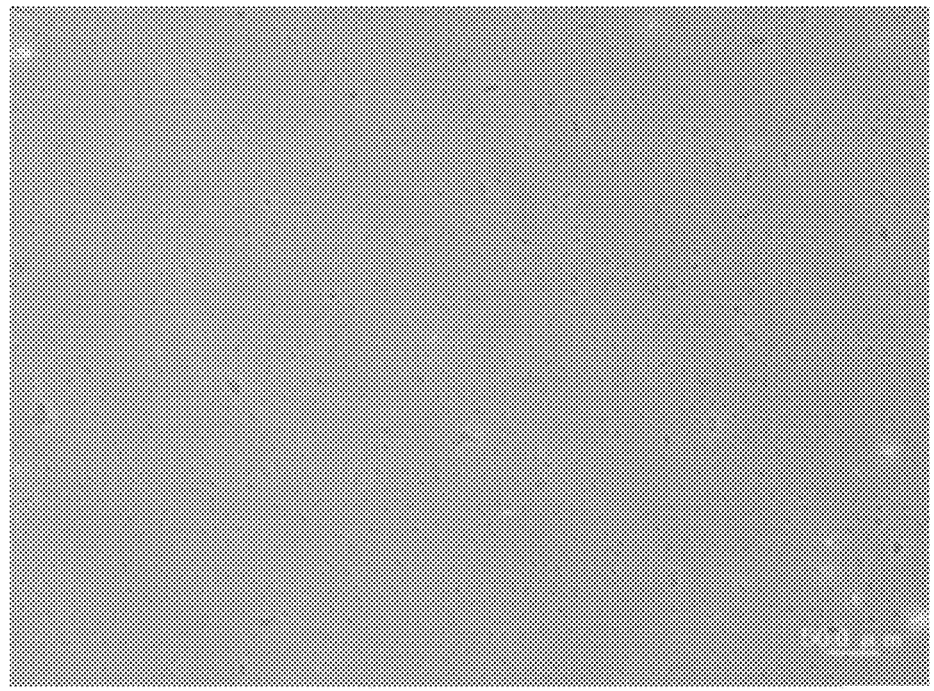
FIG. 14 shows an optical microscopic image of the suspension prepared by re-suspending the lyophilized product of Example 7 in water (×200).
Figure 15:
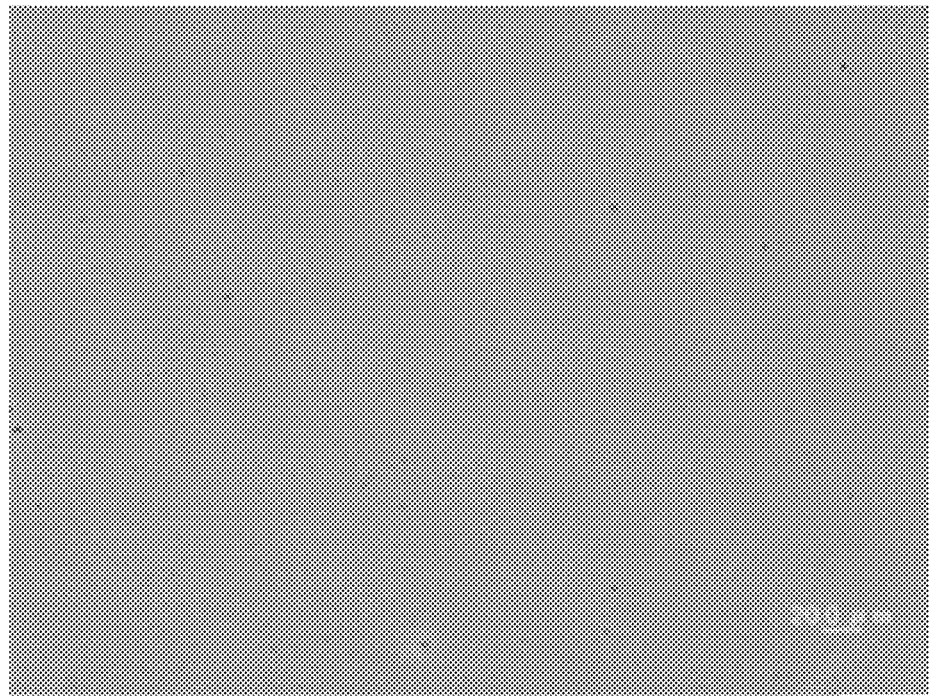
FIG. 15 shows an optical microscopic image of the pre-lyophilized suspension in Example 8 (×400).
Figure 16:
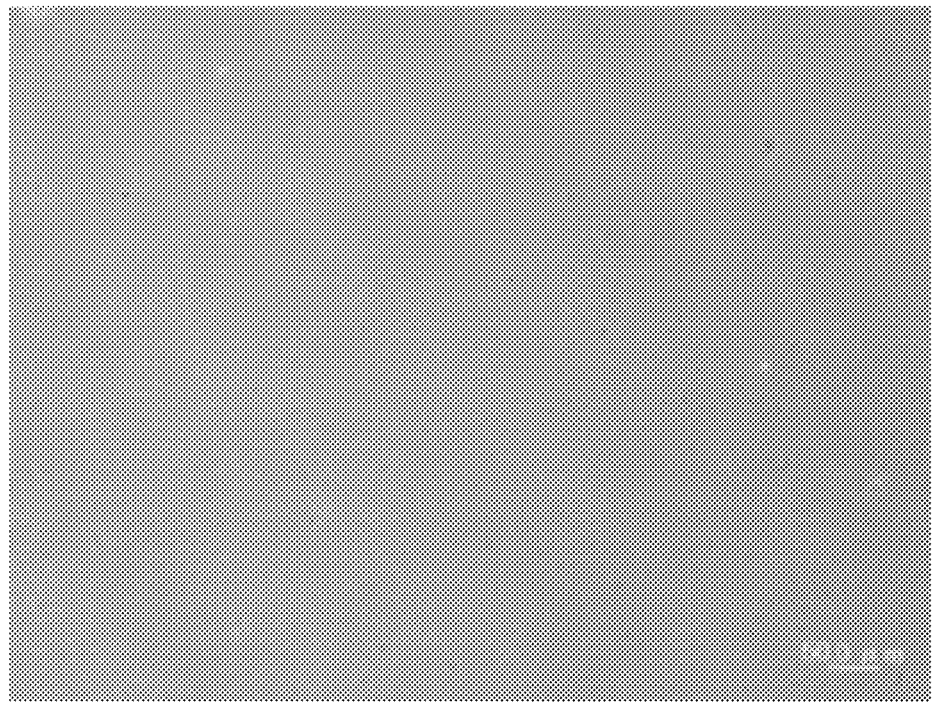
FIG. 16 shows an optical microscopic image of the suspension prepared by re-suspending the lyophilized product of Example 8 in water (×200).
Figure 17:
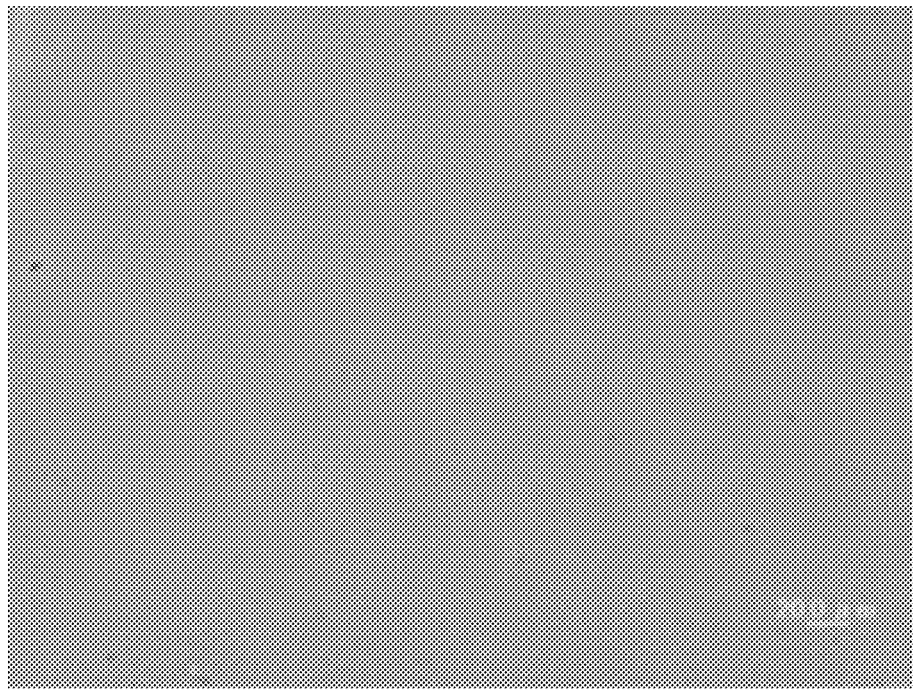
FIG. 17 shows an optical microscopic image of the pre-lyophilized suspension in Example 9 (×400).
Figure 18:
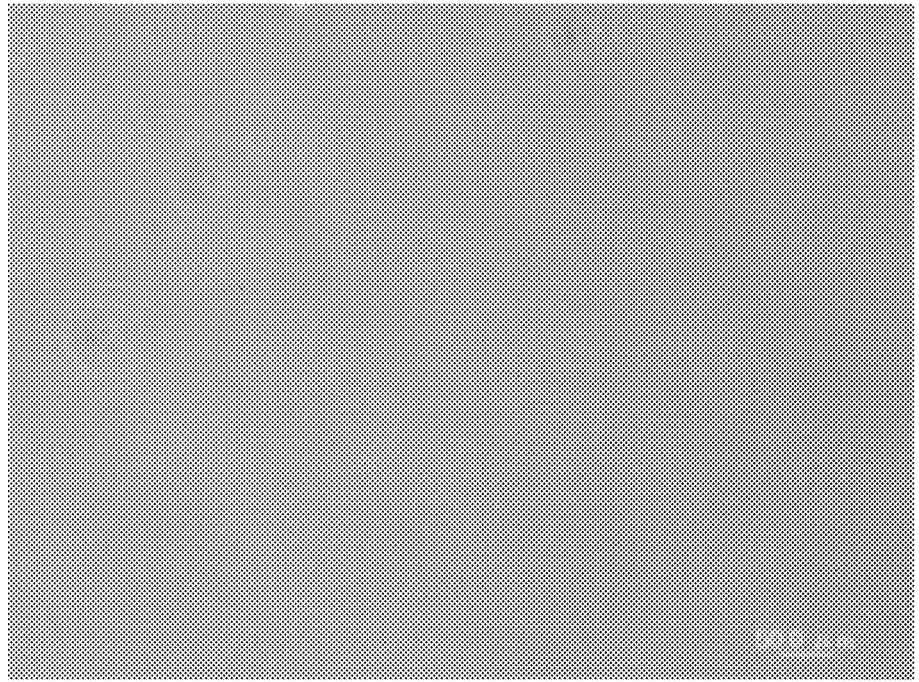
FIG. 18 shows an optical microscopic image of the suspension prepared by re-suspending the lyophilized product of Example 9 in water (×200).
Figure 19:
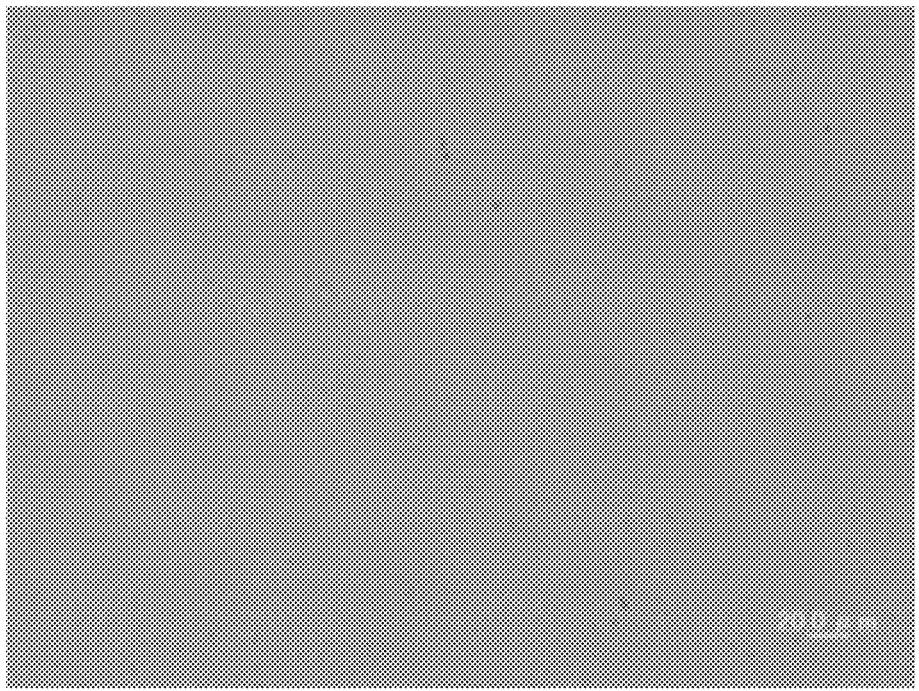
FIG. 19 shows an optical microscopic image of the pre-lyophilized suspension in Comparative example 5 (×400).
Figure 20:
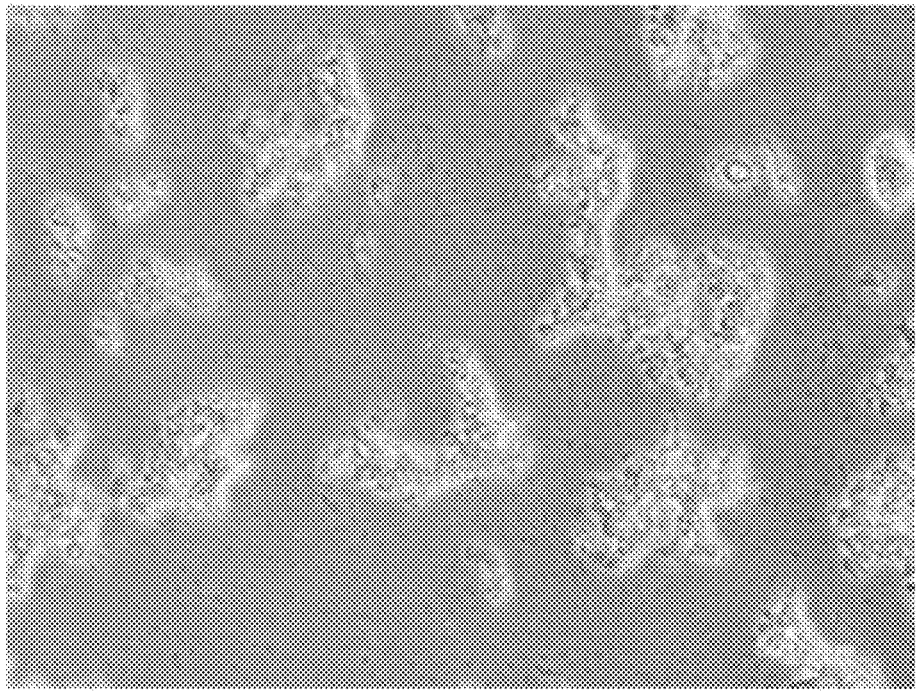
FIG. 20 shows an optical microscopic image of the suspension prepared by re-suspending the lyophilized product of Comparative example 5 in water (×200).
Figure 21:
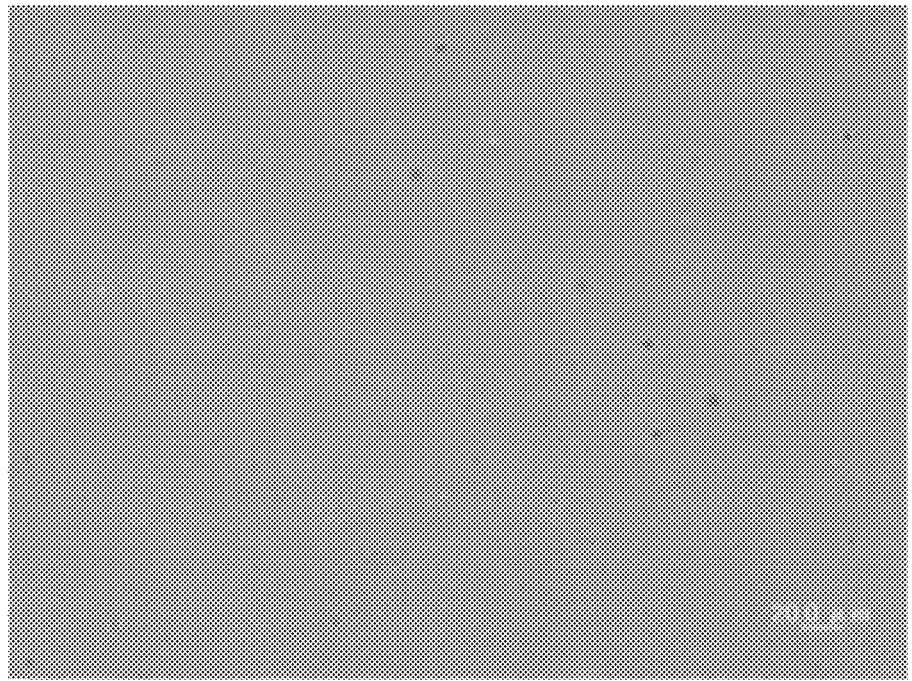
FIG. 21 shows an optical microscopic image of the pre-lyophilized suspension in Comparative example 6 (×400).
Figure 22:
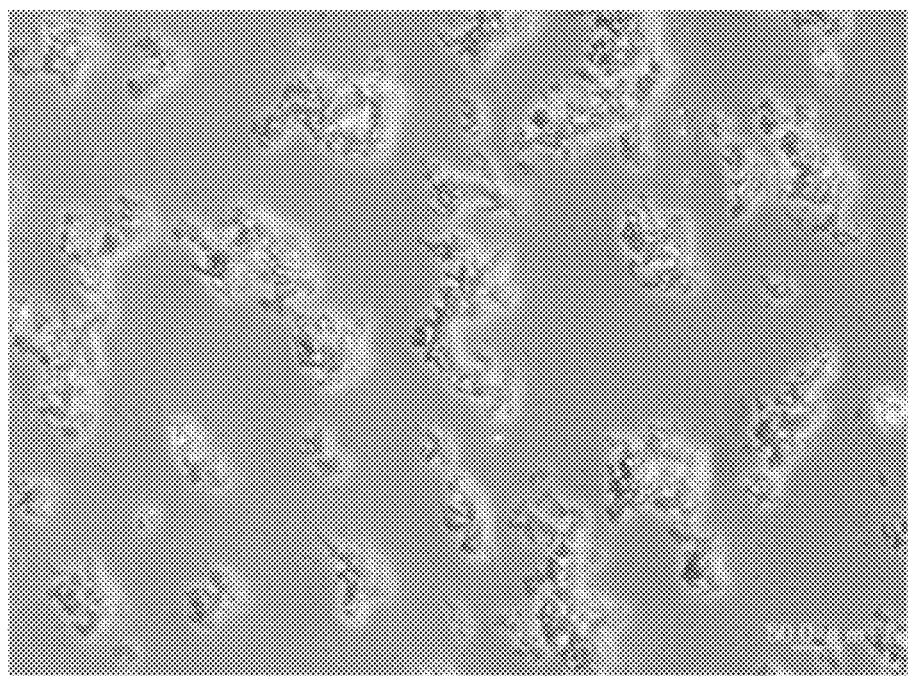
FIG. 22 shows an optical microscopic image of the suspension prepared by re-suspending the lyophilized product of Comparative example 6 in water (×200).
Figure 23:
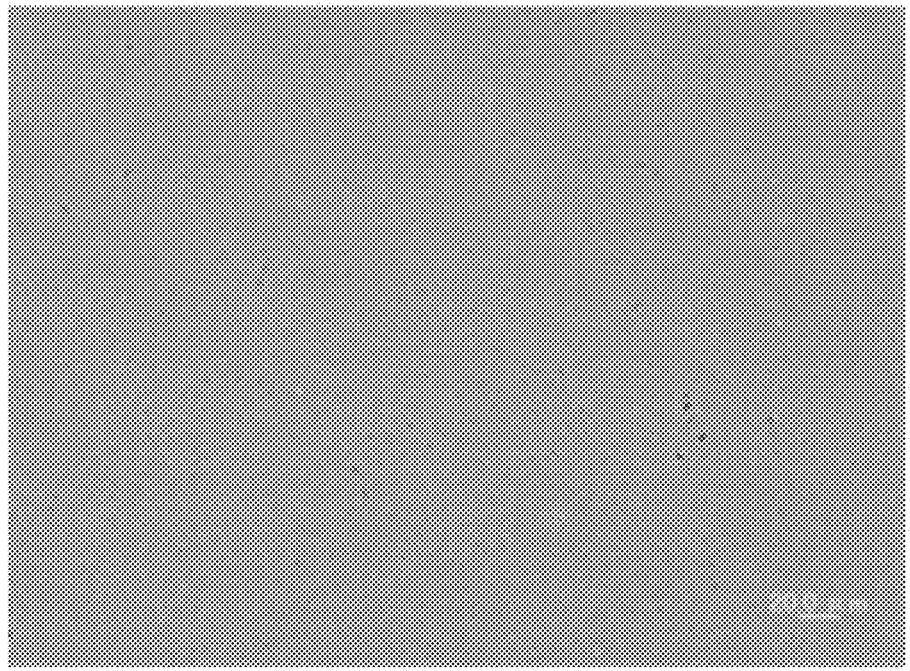
FIG. 23 shows an optical microscopic image of the pre-lyophilized suspension in Comparative example 7 (×400).
Figure 24:
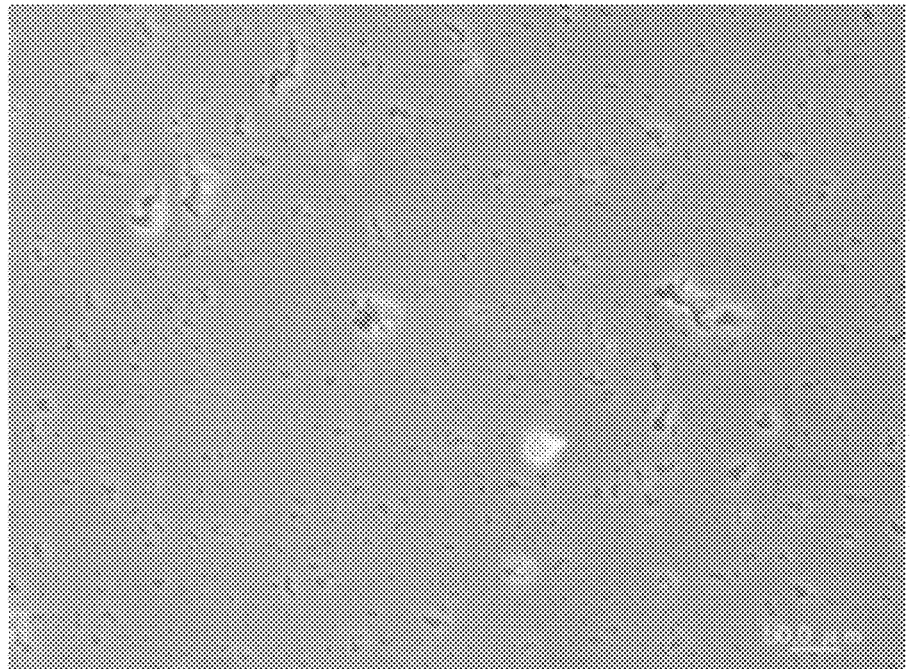
FIG. 24 shows an optical microscopic image of the suspension prepared by re-suspending the lyophilized product of Comparative example 7 in water (×200).
Figure 25:
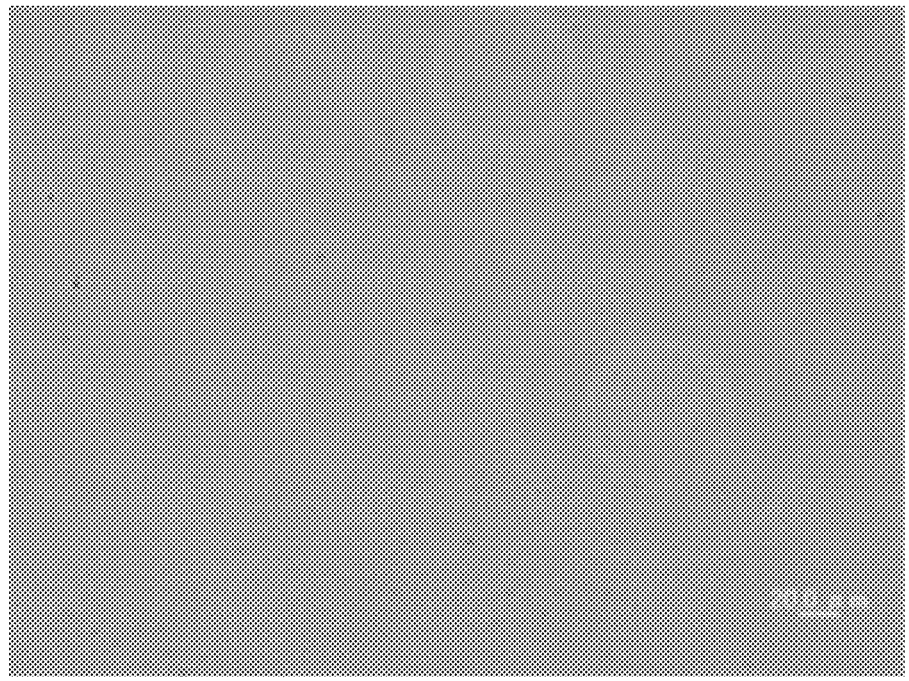
FIG. 25 shows an optical microscopic image of the pre-lyophilized suspension in Comparative example 8 (×400).
Figure 26:
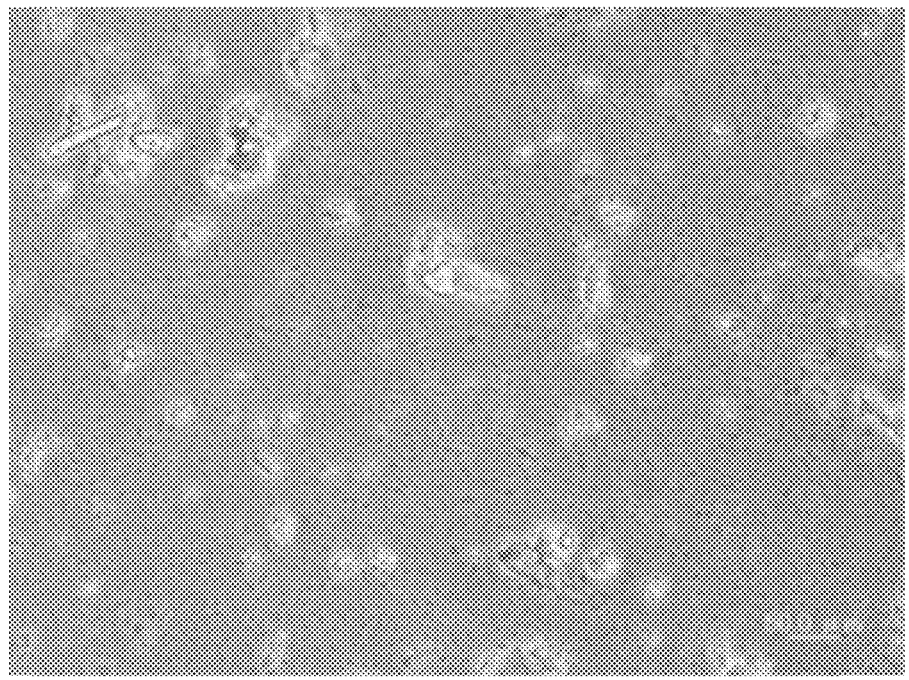
FIG. 26 shows an optical microscopic image of the suspension prepared by re-suspending the lyophilized product of Comparative example 8 in water (×200).
Figure 27:
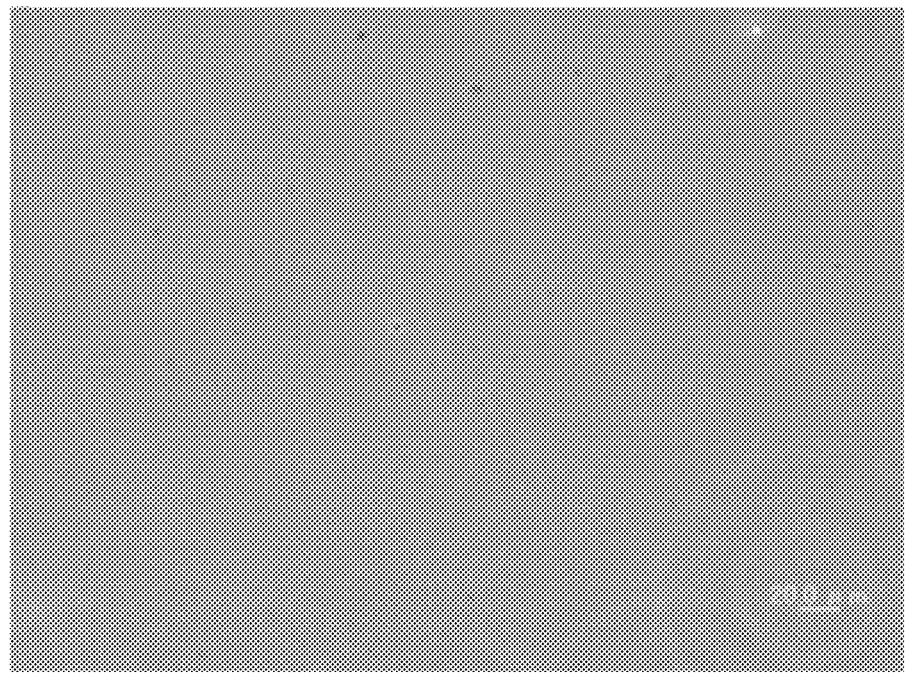
FIG. 27 shows an optical microscopic image of the pre-lyophilized suspension in Comparative example 9 (×400).
Figure 28:
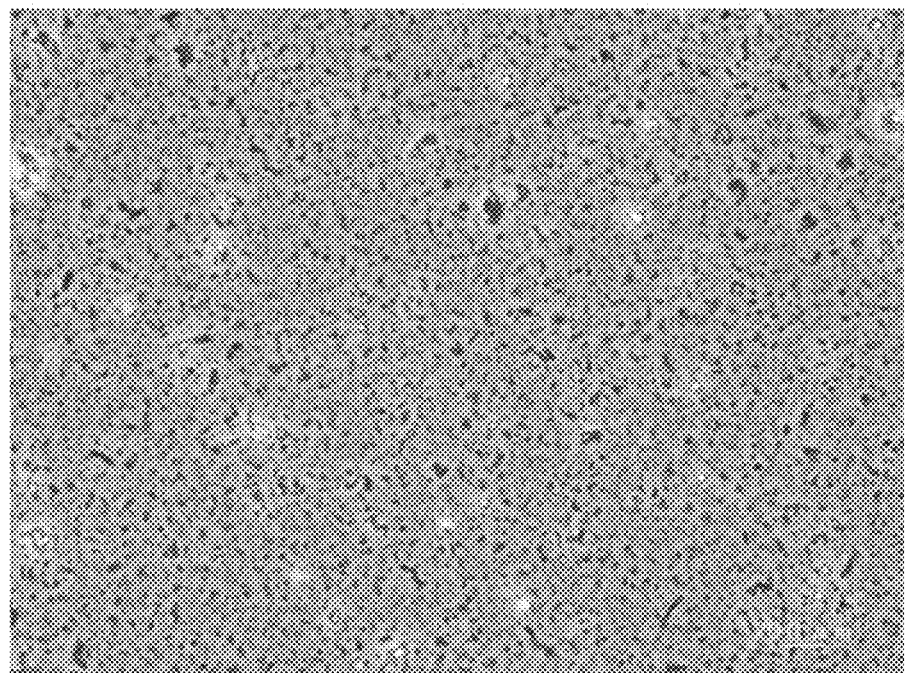
FIG. 28 shows an optical microscopic image of the suspension prepared by re-suspending the lyophilized product of Comparative example 9 in water (×400).
Figure 29:
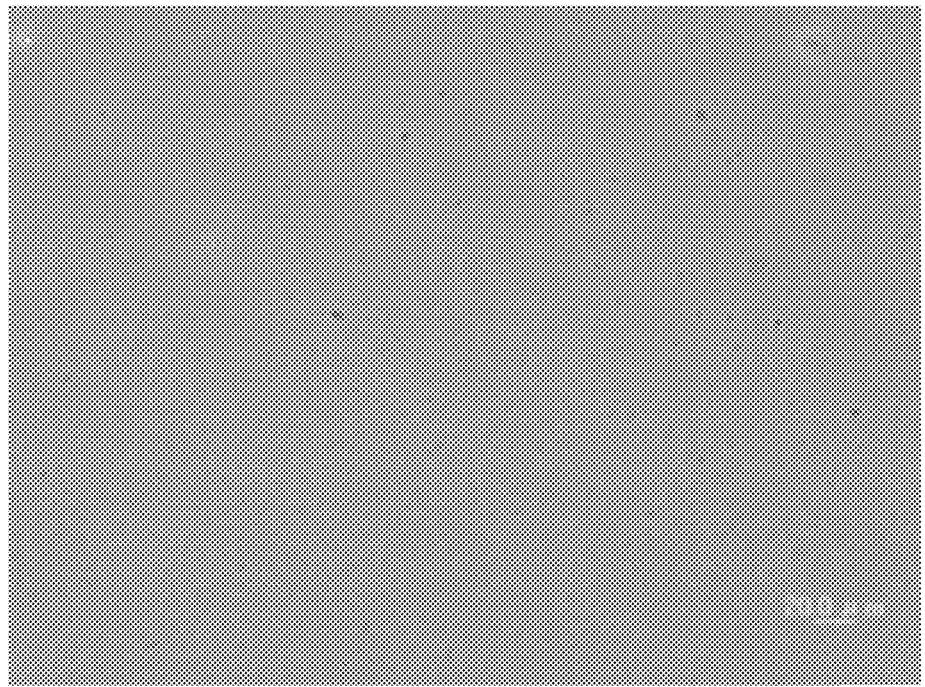
FIG. 29 shows an optical microscopic image of the pre-lyophilized suspension in Comparative example 10 (×400).
Figure 30:
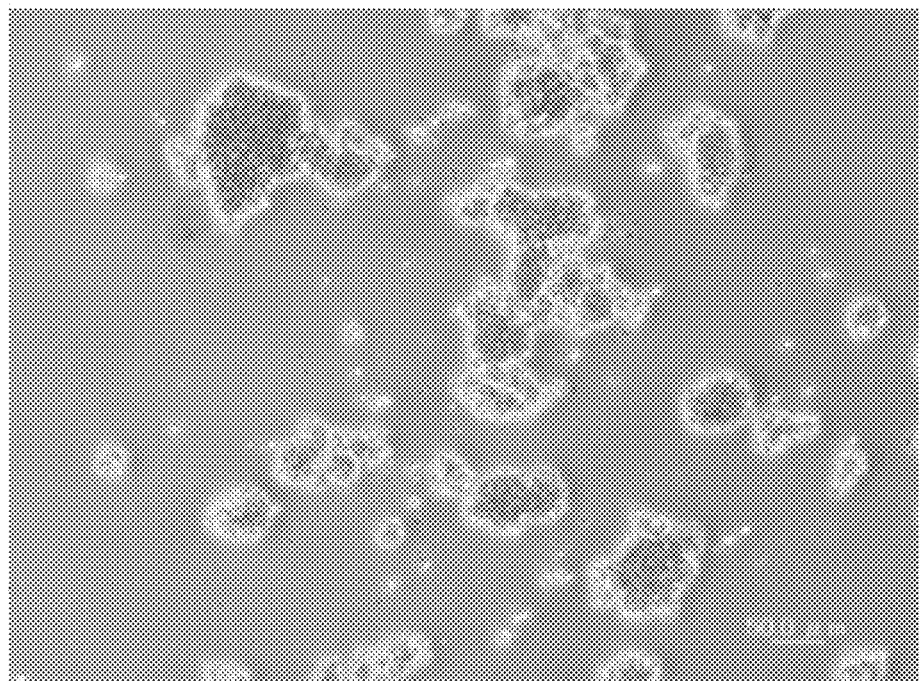
FIG. 30 shows an optical microscopic image of the suspension prepared by re-suspending the lyophilized product of Comparative example 10 in water (×200).
Figure 31:
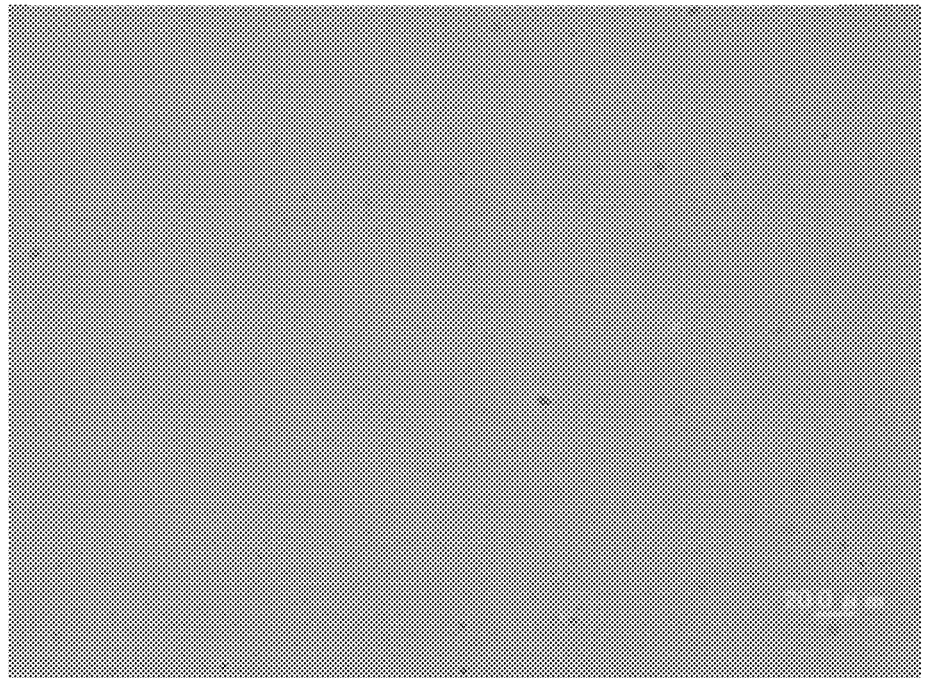
FIG. 31 shows an optical microscopic image of the pre-lyophilized suspension in Comparative example 11 (×400).
Figure 32:
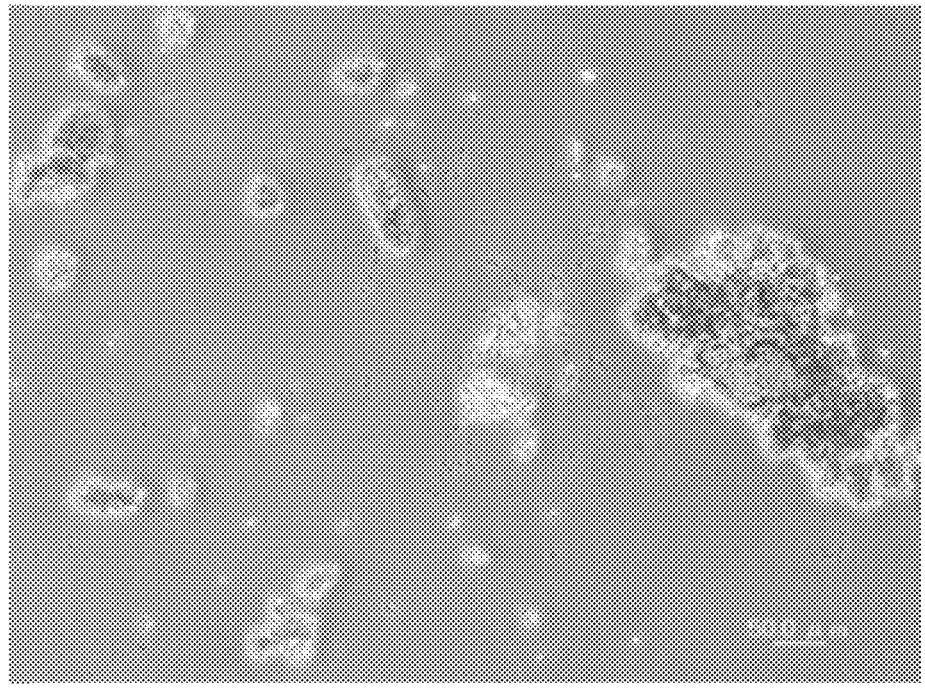
FIG. 32 shows an optical microscopic image of the suspension prepared by re-suspending the lyophilized product of Comparative example 11 in water (×200).
Figure 33:
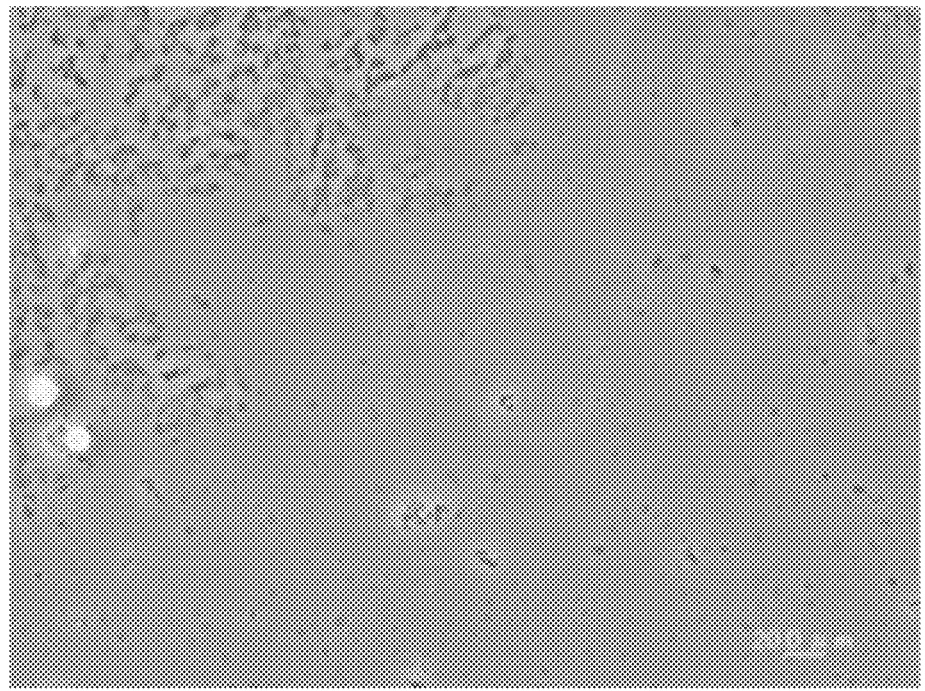
FIG. 33 shows an optical microscopic image of the pre-lyophilized suspension in Comparative example 12 (×400).
Figure 34:
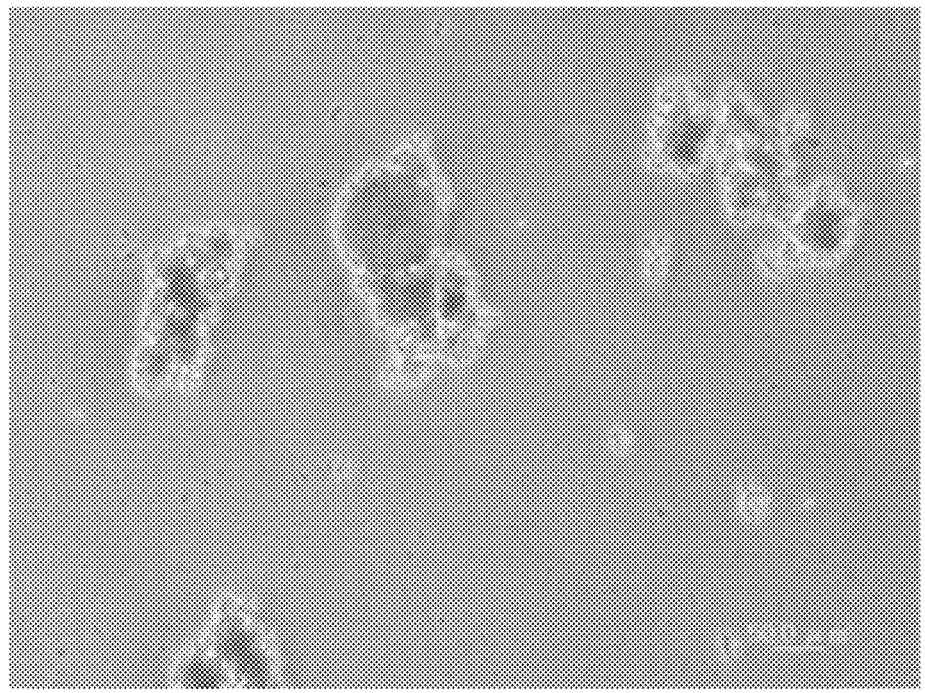
FIG. 34 shows an optical microscopic image of the suspension prepared by re-suspending the lyophilized product of Comparative example 12 in water (×200).
Figure 35:
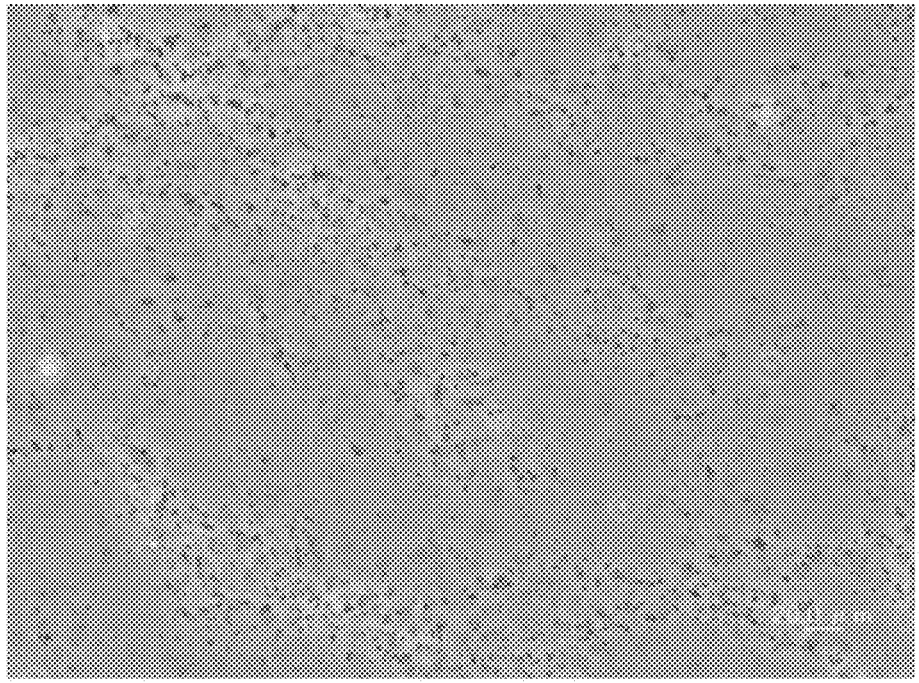
FIG. 35 shows an optical microscopic image of the pre-lyophilized suspension in Comparative example 13 (×400).
Figure 36:
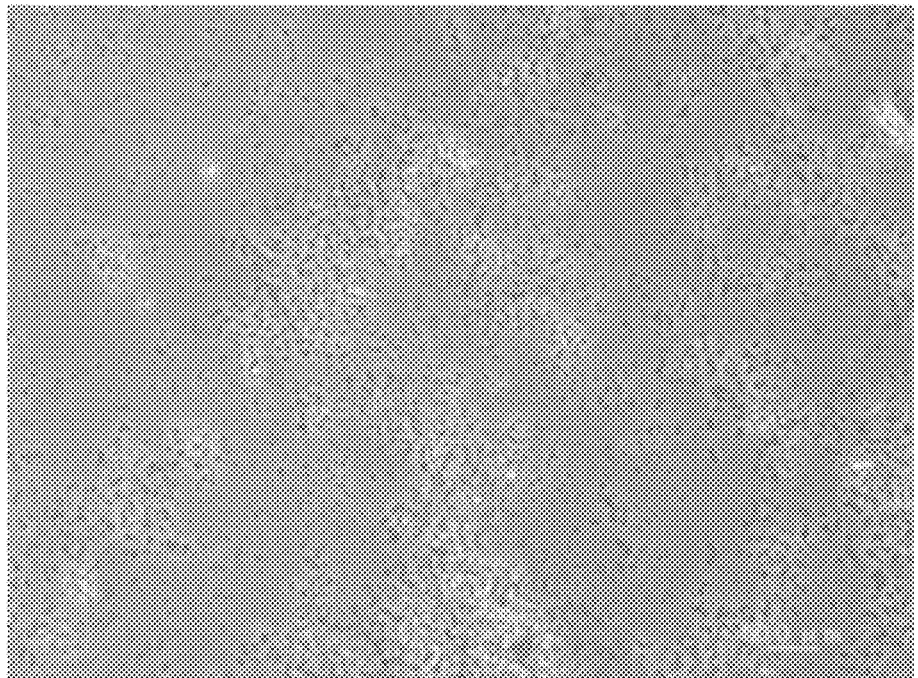
FIG. 36 shows an optical microscopic image of the suspension prepared by re-suspending the lyophilized product of Comparative example 13 in water (×200).
Figure 37:
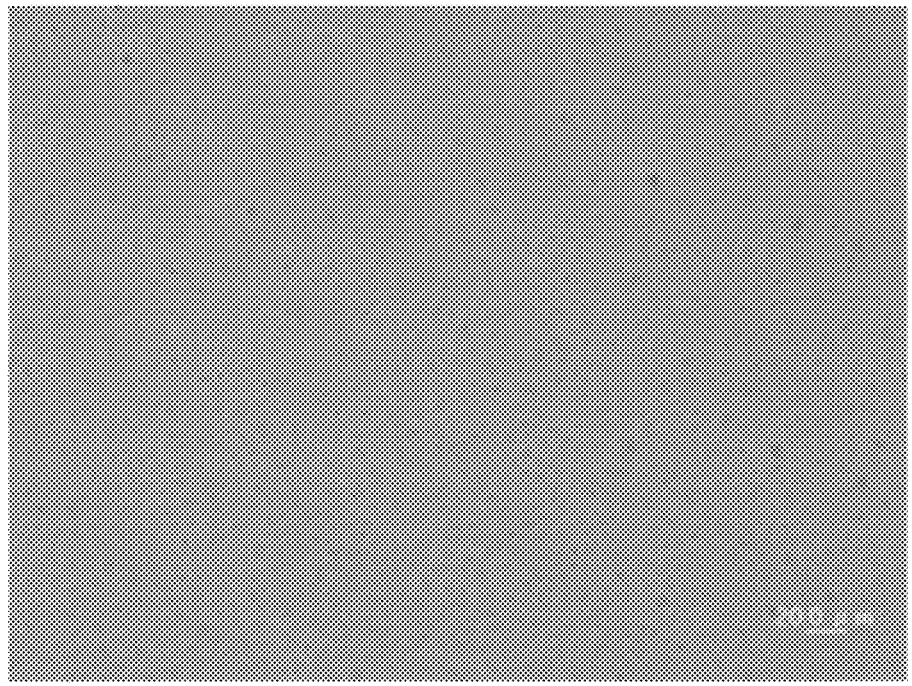
FIG. 37 shows an optical microscopic image of the pre-lyophilized suspension in Comparative example 14 (×400).
Figure 38:
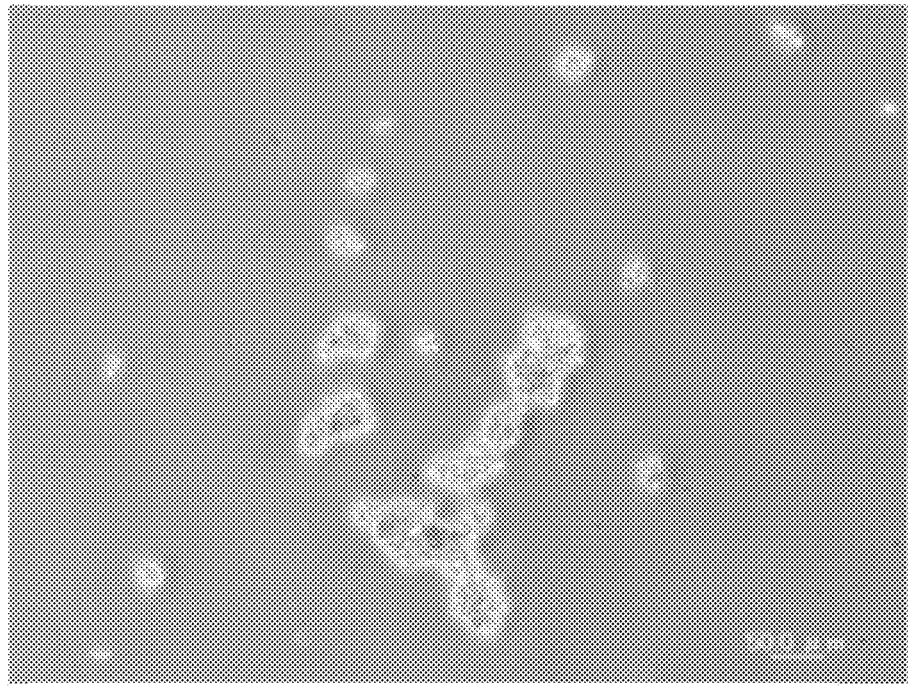
FIG. 38 shows an optical microscopic image of the suspension prepared by re-suspending the lyophilized product of Comparative example 14 in water (×200).
Figure 39:
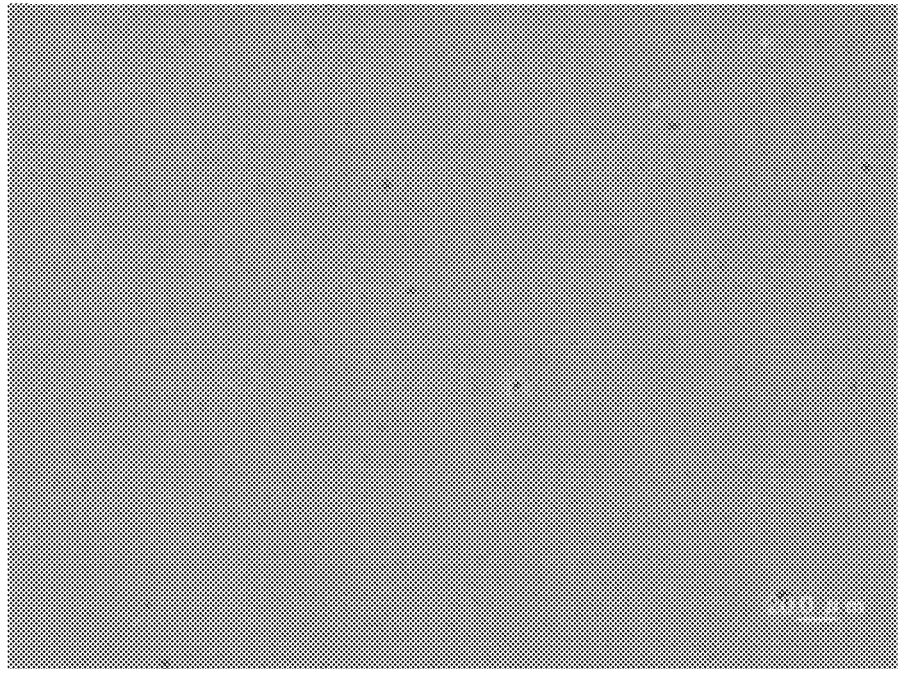
FIG. 39 shows an optical microscopic image of the pre-lyophilized suspension in Comparative example 15 (×400).
Figure 40:
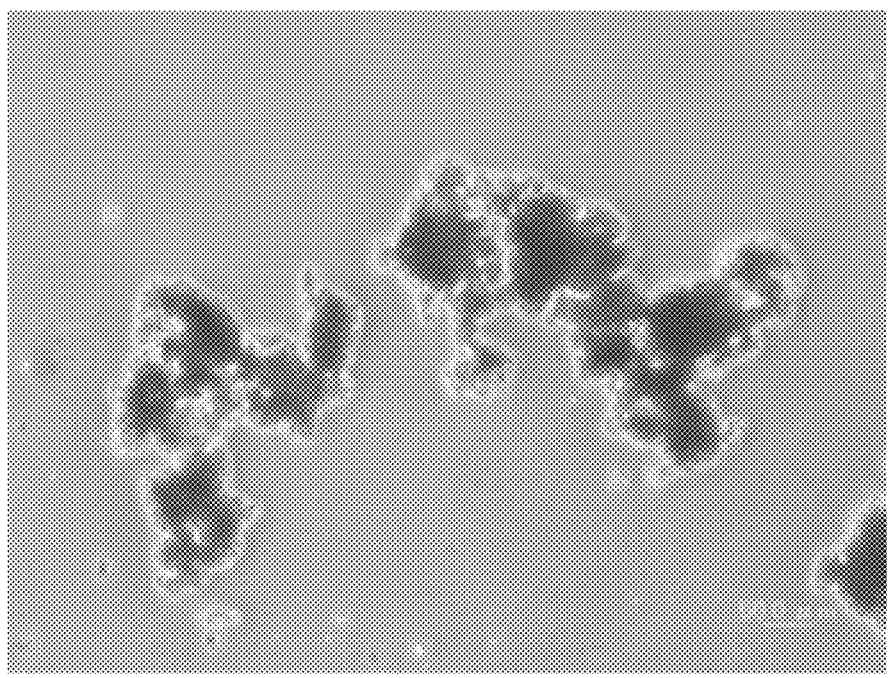
FIG. 40 shows an optical microscopic image of the suspension prepared by re-suspending the lyophilized product of Comparative example 15 in water (×200).

1. The Composition of the Present Invention

The composition of the present invention comprises (A) ingredient, (B) ingredient, and (C) ingredient, wherein the (A) is an active ingredient which is hardly soluble in water, but soluble in a $C_{1-4}$ lower alcohol that may contain 30 vol % or less water, the (B) is polyvinyl alcohol having a saponification rate of 55-99%, and the (C) is a non-ionic surfactant, wherein the (A) active ingredient has a mean particle size of 10-300 nm.

The "soluble" used herein means that an active ingredient, other excipients and the like in a solvent exist in a transparent state, and the "completely soluble" means that all ingredients in a solvent are in a soluble state.

The "hardly soluble in water" used herein means that the solubility of an active ingredient in water is 0.1 mg/mL or lower at 25° C. The "water" used herein may include a water containing a buffer agent and/or a pH adjuster, for example, when the active ingredient is dissolved in said water to give a liquid preparation, the solubility of the active ingredient is 0.1 mg/mL or lower at a suitable pH to be administered to human beings.

The "active ingredient" used herein means an organic compound having a biological activity or a pharmaceutically acceptable salt thereof. And, the organic compound having a biological activity or a pharmaceutically acceptable salt thereof may be in a hydrate form or in a solvate form, which is also included in the active ingredient.

The "active ingredient" in the present composition is an active ingredient which is hardly soluble in water, but completely soluble in a water-miscible $C_{1-4}$ organic solvent that may contain 30 vol % or less water, specifically in a $C_{1-4}$ lower alcohol that may contain 30 vol % or less water, in a concentration of 1.5 mg/mL or more, preferably 5 mg/mL or more, more preferably 10 mg/mL or more.

The active ingredient used herein should not be limited as long as the active ingredient is hardly soluble in water, but completely soluble in a water-miscible $C_{1-4}$ organic solvent that may contain 30 vol % or less water, specifically in a $C_{1-4}$ lower alcohol that may contain 30 vol % or less water, which includes, for example, antipsychotic drug, analgesic drug, cancer therapy drug, anti-inflammatory drug, antihypertensive drug, cardiovascular agent, antifungal agent, enzyme inhibitor, anxiolytic sedative drug, a drug for treating a disease in posterior eye segment such as age-related macular degeneration, and a drug for treating a disease in anterior eye segment such as dry eye. The organic compound having a biological activity which is comprised as an active ingredient of the present invention includes, for example, (R)-(−)-2-(4-bromo-2-fluorobenzyl)-1,2,3,4-tetrahydropyrrolo[1,2-a]pyrazine-4-spiro-3'-pyrrolidine-1,2',3,5'-tetraone (ranirestat, hereinafter referred to as "Compound A"), 2-(4-ethyl-1-piperazinyl)-4-(4-fluorophenyl)-5,6,7,8,9,10-hexahydrocycloocta[b]pyridine (blonanserin), and indomethacin, preferably, Compound A.

Compound A which the present composition comprises as an active ingredient may be in free form, in a salt form with a pharmaceutically acceptable inorganic or organic base, or in a hydrate or solvate form. The above salt with an inorganic base includes, for example, an alkali metal salt such as a sodium salt and a potassium salt; and an ammonium salt. The above salt with an organic base includes, for example, a salt with isopropylamine, diethylamine, ethanolamine, piperidine, lysine, or the like. The details of the above things are described in Patent Literature 4. Compound A or a pharmaceutically acceptable salt thereof can be prepared, for example, according to the processes disclosed in Patent Literature 4.

The "$C_{1-4}$ lower alcohol" used herein may be a straight or branched lower alcohol which is mono-valent or multi-valent, preferably mono-valent or bi-valent, which includes, for example, methanol, ethanol, 1-propanol, 2-propanol, 1,1-dimethylethanol, 1,2-ethanediol, 1,2-propanediol, 1,3-propanediol, and 1,2,3-propanetriol, preferably ethanol, 1-propanol, 2-propanol, and 1,1-dimethylethanol.

The mean particle size of an active ingredient in the present composition is 10 nm-300 nm, preferably 10 nm-200 nm, more preferably 10 nm-150 nm, even more preferably 10 nm-100 nm, particularly preferably 10 nm-50 nm.

With regard to the particle size distribution of an active ingredient in the present composition, preferably the D90 particle size is 300 nm or less, more preferably the D90 particle size is 250 nm or less, even more preferably the D90 particle size is 220 nm or less, particularly preferably the D90 particle size is 200 nm or less.

The "suspension composition" used herein means that a fine particle of an active ingredient is in a suspension state in a liquid, which also includes an apparent solution-state but having suspended fine particles.

When the present composition is a suspension composition, the mean particle size and particle size distribution of a fine particle of an active ingredient suspended in a liquid can be measured by light scattering method. The mean particle size used herein denotes median diameter based on the intensity of scattered light measured by light scattering method (also referred to as 50% diameter to D50 particle size), which is a median diameter of a solid active ingredient suspended in a suspension composition or a median diameter of an active ingredient held in a solid composition, in which the mean particle size in a suspension composition means a mean particle size of an active ingredient which exists in a solid state in a suspension composition.

And, D90 particle size for indicating a particle size distribution is an index value indicating the particle size distribution of a fine particle which is obtained by light scattering method, and it denotes the particle size of the biggest fine particle at the time that the amount of particles accumulated from the smallest fine particle reaches 90%. The "D90 particle size" used herein denotes a particle size calculated on the basis of the scattering light intensity, which is a D90 particle size of a solid active ingredient suspended in a suspension or a D90 particle size of an active ingredient held in a dried solid, in which the D90 particle size in a suspension means a D90 particle size of an active ingredient which exists in a solid state in a suspension.

The mean particle size and the D90 particle size can be measured with a measuring instrument, Zetasizer Nano S (Malvern Instruments Ltd.) or the like. In case that a suspension to be measured is highly concentrated, the suspension may be diluted to a measurable range of the concentration.

In detail, the particle size of a solid active ingredient dispersed in a suspension composition, for a particle size of 1 nm-5 µm, preferably 10 nm-5 µm, can be obtained by deluting the sample with a diluting solvent whose amount is a suitable to the amount of the suspension composition, for example, 100 parts of the solvent and then measuring the diluted sample with a measuring instrument; Zetasizer Nano S (Malvern Instruments Ltd.), in which Material RI is 1.5, Dispersant RI is 1.33, and Sample Viscosity is 0.9. The particle size may be also obtained from the average of plural measurements of one identical sample, for example, from three-repeated measurements.

When the present composition is a solid composition, the mean particle size or particle size distribution thereof may be measured in the same manner mentioned in the above suspension composition after suspending the solid composition in an aqueous dispersion media which is described below.

The "polyvinyl alcohol" used herein is a polymer of polyvinyl acetate in which partial or all units of polyvinyl acetate are saponified to hydroxy groups.

The "saponification rate" used herein denotes a ratio of the hydroxy unit in the polyvinyl alcohol molecule per the total units of hydroxy group and acetate group in the polyvinyl alcohol molecule.

The "polyvinyl alcohol having a saponification rate of 55-99%" used in the present composition includes a polyvinyl alcohol whose saponification rate is preferably 60%-95%, more preferably 70%-95%, more preferably 80%-95%, even more preferably 80%-90%. The molecular weight of polyvinyl alcohol having a saponification rate of 55-99% should not be limited to a specific one, but preferably 150000 or lower, more preferably 100000 or lower, even more preferably 50000 or lower. The molecular weight of polyvinyl alcohol in the present invention means its mean molecular weight thereof, for example, polyvinyl alcohol having a molecular weight of 150000 or lower means that the mean molecular weight of the used polyvinyl alcohol is 150000 or lower.

The content of polyvinyl alcohol having a saponification rate of 55-99% used in the present composition is 0.2 parts or more by weight, more preferably 0.5 parts or more by weight, more preferably 0.5-5 parts by weight, more preferably 0.8-5 parts by weight, even more preferably 0.8-3 parts by weight, per 1 part by weight of the active ingredient.

Polyvinyl alcohol may be obtained from commercial products, for example, it is commercially available as trade names, Gohsenol™ EG-05, Gohsenol EG-40 (Nippon Synthetic Chemical Industry Co., Ltd.), J-POVAL™ JP-05, J-POVAL JP-18 (JAPAN VAM & POVAL CO., LTD.), PVA5-88 EMPROVE PhEur, USP, JPE, PVA18-88 EMPROVE PhEur, USP, JPE (Merck), etc.

The surfactant used herein should not be limited as long as it is a material which has both of a hydrophilic group and a hydrophobic group (lipophilic group) in its molecular, which can form a micell, vesicle, or lamellar structure when its concentration is higher than a certain one; which has an action to reduce surface tension, and which has an action to inhibit the crystal growth of a fine particle of an active ingredient or the aggregation thereof. The surfactant used herein includes, for example, polyoxyethylene sorbitan fatty acid ester (such as polysorbate 80, polysorbate 65, polysorbate 60, polysorbate 40, and polysorbate 20), polyoxyethylene hydrogenated castor oil (such as polyoxyethylene hydrogenated castor oil 5, polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, and polyoxyethylene hydrogenated castor oil 100), polyoxyethylene castor oil (such as CO-3 and CO-10), benzalkonium chloride, alkyldiaminoethylglycine hydrochloride, sodium deoxycholate, octylphenol ethoxylate, polyvinyl alcohol (partially saponified form), polyvinyl alcohol (completely saponified form), polyethylene glycol monostearate (such as polyoxyl 55 stearate, polyoxyl 45 stearate, and polyoxyl 40 stearate), glycerin, propylene glycol, sodium chondroitin sulfate, aluminium monostearate, alkylallyl polyether alcohol, cholesterol, sucrose fatty acid ester, sorbitan fatty acid ester, sorbitan monostearate, sorbitan monooleate, sorbitan sesquioleate, glyceryl monooleate, glyceryl monostearate, sorbitan sesquioleate, stearic acid, oleic acid, stearyl alcohol, oleyl alcohol, cetanol, cetomacrogol 1000, diethyl sebacate, sodium dodecylbenzenesulfonate, sodium lauryl sulfate, sorbitan trioleate, nonylphenoxy polyoxyethylene ethane-sulfate ester ammonium, polyoxyethylene oleyl amine, polyoxyethylene stearyl ether, polyoxyethylenecetyl ether, polyoxyethylene sorbitan monolaurate, polyoxyethylene sorbitol beeswax, polyoxyethylene nonylphenylether, polyoxyethylene polyoxypropylene glycol (such as polyoxyethylene (3) polyoxypropylene (17) glycol, polyoxyethylene (20) polyoxypropylene (20) glycol, polyoxyethylene (30) polyoxypropylene (35) glycol, polyoxyethylene (42) polyoxypropylene (67) glycol, polyoxyethylene (54) polyoxypropylene (39) glycol, polyoxyethylene (105) polyoxypropylene (5) glycol, polyoxyethylene (120) polyoxypropylene (40) glycol, polyoxyethylene (160) polyoxypropylene (30) glycol, polyoxyethylene (196) polyoxypropylene (67) glycol, polyoxyethylene (200) polyoxypropylene (70) glycol, and polyoxyethylene (240) polyoxypropylene (60) glycol), polyoxyethylene polyoxypropylene cetyl ether (such as polyoxyethylene (1) polyoxypropylene (1) cetyl ether, polyoxyethylene (10) polyoxypropylene (4) cetyl ether, polyoxyethylene (17) polyoxypropylene (23) cetyl ether, polyoxyethylene (20) polyoxypropylene (4) cetyl ether, and polyoxyethylene (20) polyoxypropylene (8) cetyl ether), hydrogenated soybean phosphatidylcholine, dimyristoylphosphatidylcholine, dipalmitoyl phosphatidylcholine, distearylphosphatidylcholine, polyvinyl caprolactam-polyvinyl acetate-polyethylene glycol graft copolymer (commercially available as a commercial name of Soluplus from BASF in Japan), poly(2-methacryloyloxy phosphorylcholine)-poly(n-butyl methacrylate) (commercially available as a commercial name of PUREBRIGHT MB-37-50T or PUREBRIGHT MB-37-100T from NOF CORPORATION), lauromacrogol, macrogol 400, macrogol 4000, macrogol 6000, lauryl dimethylamine oxide solution, lauric acid diethanolamide, sodium lauroylsarcosinate, sodium polyoxyethylene laurylether phosphate, and polyoxyethylene oleylether phosphate.

Preferably, it includes a non-ionic surfactant which has no ionicity in water. The non-ionic surfactant used herein includes, for example, polyoxyethylene sorbitan fatty acid ester, polyoxyethylene hydrogenated castor oil, polyoxyethylene castor oil, polyvinyl alcohol (partially saponified form), octylphenol ethoxylate, sorbitan fatty acid ester, sorbitan monostearate, sorbitan monooleate, sorbitan sesquioleate, glyceryl monooleate, glyceryl monostearate, polyoxyethylene polyoxypropylene glycol, and polyoxyethylene polyoxypropylene cetyl ether.

More preferably, it includes polyoxyethylene polyoxypropylene glycol, polyoxyethylene hydrogenated castor oil, polyoxyethylene castor oil, polyoxyethylene sorbitan fatty acid ester, polyethylene glycol monostearate, sorbitan monooleate, sorbitan sesquioleate, glyceryl monooleate, and polyvinyl alcohol having a saponification rate of less than 55% (partially saponified form).

Even more preferably, it includes polysorbate 80, polyoxyethylene hydrogenated castor oil 60, and polyoxyethylene polyoxypropylene glycol comprising polyoxyethylene units in 40-80 wt % (for example, polyoxyethylene (240) polyoxypropylene (60) glycol, polyoxyethylene(200) polyoxypropylene (70) glycol, polyoxyethylene (160) polyoxypropylene (30) glycol, and polyoxyethylene (30) polyoxypropylene (35) glycol).

And, not only one surfactant, but two or more surfactants may be used, preferably 2-3 surfactants.

Polyoxyethylene polyoxypropylene glycol may be obtained from commercial products, for example, it is commercially available as trade names, Unilube™ 70DP-950B, Unilube 75DE-2620R, PLONON #188P (NOF COR- PORATION), Kolliphor P188, Kolliphor P407 (BASF in Japan), Pluronic™ F-68 (Sigma-Aldrich Japan), etc.

The content of surfactant used in the present composition is 0.02-0.8 parts by weight, preferably 0.02-0.7 parts by weight, preferably 0.02-0.6 parts by weight, 0.02-0.45 parts by weight, more preferably 0.02-0.35 parts by weight, more preferably 0.025-0.3 parts by weight, more preferably 0.03-0.2 parts by weight, even more preferably 0.03-0.1 parts by weight, per 1 part by weight of the active ingredient.

The suspension composition of the present invention may further comprise poly(2-methacryloyloxy phosphorylcholine)-poly(n-butyl methacrylate) (hereinafter, referred to as "MPC polymer"). The MPC polymer used herein should not be limited, and preferably it is an MPC polymer having a molecular weight of 30000 or more.

The content of MPC polymer is 0.01-1 parts by weight, preferably 0.05-0.6 parts by weight, more preferably 0.05-0.5 parts by weight, even more preferably 0.05-0.4 parts by weight, per 1 part by weight of the active ingredient.

Poly(2-methacryloyloxy phosphorylcholine)-poly(n-butyl methacrylate) may be obtained from commercial products, for example, it is commercially available as trade names, PUREBRIGHT MB-37-50T, PUREBRIGHT MB-37-100T (NOF CORPORATION), etc.

2. Suspension Composition as Manufacturing Intermediate

The composition of the present invention may comprise the (D) ingredient, besides the (A) ingredient, the (B) ingredient, and the (C) ingredient, said (D) ingredient is a mixed solution comprising a water-miscible $C_{1-4}$ organic solvent and water whose water content is 50 vol % or more, preferably 65 vol % or more, wherein the (A) active ingredient in the (D) mixed solution is a manufacturing intermediate which is kept in a suspension state.

The "suspension state" used herein denotes that an active ingredient is dispersed in a liquid as in a solid state, wherein the solid state means a state of crystal, amorphia, or crystal/amorphia mixture. Also, it includes a state that an active ingredient is partially dissolved in a liquid. In addition, it includes a state that an active ingredient precipitates or aggregates under a storage, but can be back to suspension state by shaking it before use. However, the suspension state of the present invention does not include a state that includes molecular assembly such as liposome or matrix of polymer.

The "kept in XXX" used herein means that an active ingredient is kept about the shape of its fine particle or its particle size. In case that an active ingredient is in a liquid, it may include a state that the active ingredient in the liquid is kept in a suspension state without quick aggregation of its fine particle having a given shape and particle size. In case that the active ingredient in a solid, it may include a state that the active ingredient in the solid is kept in a suspension state without quick aggregation of its fine particle having a given shape and particle size. That is, the term denotes that the particle size of a fine particle of an active ingredient which is re-suspended in a dispersion media such as water is kept compared with the suspension state of the pre-solidified one.

The content of the (A) active ingredient in the present suspension composition which also comprises the (D) ingredient is 1.5-100 mg/mL, preferably 1.5-50 mg/mL, more preferably 1.5-40 mg/mL, more preferably 1.5-20 mg/mL, even more preferably 1.5-20 mg/mL, particularly preferably 1.5-10 mg/mL, but not necessarily limited to these range.

In the above-mentioned suspension composition, the ratio of the dissolved active ingredient is generally 0.001%-10% of the whole of the active ingredient in the suspension composition. From the viewpoint of chemical stability and physical stability of particle size or the like, it is preferably 0.001%-5%, more preferably 0.001%-2%, more preferably 0.001%-1%, even more preferably 0.001%-0.5%, particularly preferably 0.001%-0.1%.

In the present suspension composition comprising the (D) ingredient, the content of polyvinyl alcohol is 1 mg/mL or more, preferably 2 mg/mL or more, more preferably 5 mg/mL or more, more preferably 7.5 mg/mL or more, even more preferably 7.5 mg/mL-20 mg/mL.

In the present suspension composition comprising the (D) ingredient, the content of the surfactant is 0.2 mg/mL or more, preferably 0.3 mg/mL or more, more preferably 0.3 mg/mL-7 mg/mL, more preferably 0.3 mg/mL-5 mg/mL, more preferably 0.3 mg/mL-3 mg/mL, more preferably 0.4 mg/mL-3 mg/mL, even more preferably 0.4 mg/mL-2 mg/mL.

In the present suspension composition comprising the (D) ingredient, the content of the MPC polymer is 0.3 mg/mL-10 mg/mL, preferably 0.5 mg/mL-5 mg/mL, more preferably 1 mg/mL-3 mg/mL, even more preferably 1.5 mg/mL-3 mg/mL.

3. Process to Prepare a Suspension Composition of the Present Invention

The present invention includes a process to prepare a suspension composition in which a fine particle of (A) active ingredient which is hardly soluble in water, but completely soluble in a water-miscible $C_{1-4}$ organic solvent that may contain 30 vol % or less water and whose mean particle size is 10-1000 nm (preferably 10-300 nm, more preferably 10-200 nm) is kept in a suspension state. That is, the process includes a process mixing a water-miscible $C_{1-4}$ organic solvent containing (A) active ingredient and a water solution containing (B) polyvinyl alcohol having a saponification rate of 55-99%.

The method for mixing a water-miscible $C_{1-4}$ organic solvent which is good solvent and water which is poor solvent can be done with a batch-type mixer such as magnetic stirrer and paddle mixer, or a continuous mixer such as static mixer, micro mixer, and forced thin film mixer. The condition of mixing is not limited to specific ones, but, for example, the stirring rate can be 100-2000 rpm in the process with a magnetic stirrer, and the feed rate can be 3-500 mL/min in the process with a forced thin film mixer.

The water-miscible $C_{1-4}$ organic solvent should not be limited as long as it is a water-miscible $C_{1-4}$ organic solvent or a mixture of the organic solvent and water, in which an active ingredient can be completely dissolved, for example, it includes $C_{1-4}$ lower alcohol such as methanol, ethanol, 1-propanol, 2-propanol, 1,1-dimethylethanol, 1,2-ethanediol, 1,2-propanediol, 1,3-propanediol, and 1,2,3-propanetriol; acetonitrile; acetone; dimethylsulfoxide; tetrahydrofuran; and the aforementioned solvent containing 30 vol % or less water. Preferably, it includes ethanol, 1-propanol, 2-propanol, 1,1-dimethylethanol, acetone, and a mixture of the organic solvent and water which contains 30 vol % or less water. In addition, two or more organic solvents may be used.

The suspension composition of the present invention can be prepared by mixing a good solvent containing an active ingredient and a poor solvent containing a polyvinyl alcohol. Provided that either the good solvent or the poor solvent or both thereof should also contain a surfactant, preferably a non-ionic surfactant.

Preferably, the present suspension composition can be prepared by mixing a $C_{1-4}$ lower alcohol containing an active ingredient and a surfactant, and water containing a polyvinyl alcohol having a saponification rate of 55-99%. The surfactant used herein is mentioned above.

In the present process, MPC polymer may be also added thereto. MPC polymer may be added to any of a good solvent and a poor solvent as long as the MPC polymer is dissolved therein, but preferably it is added to a poor solvent (water).

Preferably, the present suspension can be prepared by mixing a $C_{1-4}$ lower alcohol containing an active ingredient and a surfactant, and water containing a polyvinyl alcohol having a saponification rate of 55-99% and MPC polymer. The MPC polymer used herein is mentioned above.

In addition, the good solvent and/or poor solvent used in the present process may optionally comprise an excipient in a amount not to affect the particle size of an active ingredient.

By using a device such as ultrafilter and centrifuge, the solvent in which a fine particle of an active ingredient is suspended can be replaced with another solvent.

The temperature of the liquid at the time of mixing should not be limited unless the crystal growth develops. It includes preferably 1 to 30° C., more preferably 1 to 25° C., even more preferably 1 to 20° C., particularly preferably 1 to 10° C.

The time of the mixing should not be limited unless the crystal growth develops. It may be stirred for preferably 1 minute or more, more preferably 3 minutes or more, even more preferably 5 minutes or more, more preferably 10 minutes or more, particularly preferably 20 minutes or more.

4. Process to Prepare a Solid Composition of the Present Invention

The solid composition comprising a fine particle of an active ingredient having the above-mentioned particle size can be prepared by drying the suspension composition prepared in the above process, for example, by drying the suspension composition comprising the (D) ingredient. The method for drying the suspension should not be limited as long as the above-mentioned solvent can be removed. Preferably it includes drying in vacuo, more preferably lyophilization is chosen. The condition of lyophilization should not be limited as long as a cosolvent can be sublimated, for example, in using lyophilizer, the above suspension composition is frozen between −40° C. to −80° C., and then water or 1,1-dimethylethanol can be sublimated at about −20° C. under a pressure of about 10 pascal. Further, water or 1,1-dimethylethanol adhering to the solid can be volatilized at about 30° C. under a pressure of about 1 pascal to prepare a solid composition comprising a fine particle of an active ingredient.

5. Pharmaceutical Composition

The above-mentioned solid composition of the present invention, and a suspension composition in which the solid composition is suspended in an aqueous dispersion media are useful as a pharmaceutical product (pharmaceutical composition). In an embodiment, the composition of the present invention is administered as a suspension composition. In case of a solid pharmaceutical composition, it can be suspended in an aqueous dispersion media to prepare an administration liquid thereof which is a suspension pharmaceutical composition. The administration route of the present pharmaceutical composition should not be limited, but it may be administered through an administration route that a skilled person well knows. For example, the present suspension pharmaceutical composition can be administered as a liquid composition which is in a suspension state, by injection, eye drop, nasal drop, transdermal administration or pulmonary administration.

In addition, the pharmaceutical composition of the present invention also includes an embodiment that an active ingredient and an aqueous dispersion media are separately provided and then the active ingredient or a physiologically acceptable salt thereof is suspended in the aqueous dispersion media when used (i.e., kit), for example, a kit comprising (1) a solid pharmaceutical composition comprising a fine particle of an active ingredient and (2) a dispersion media is also an embodiment of the present invention. And, it is possible to provide a suspension composition and a dispersion media for diluting the suspension composition with the dispersion media. The formulation of the present invention also includes a formulation which is used up in one shot or in a week or other periods, and a formulation of preparing a suspension in use whose use is limited to a week, a month, or other periods after preparing a suspension.

On the other hand, in case that the present solid pharmaceutical composition is administered as in a solid state, it is possible to administer the solid pharmaceutical composition prepared in the above manner in a condition that retains a fine particle of an active ingredient, and also it is possible to administer it as a drug formulation such as a tablet and a powder which is prepared through dry granulation, fluid-bed granulation, tableting, etc. The administration route of the solid pharmaceutical composition should not be limited, but oral administration or the like is available.

The "aqueous dispersion media" used herein is an aqueous dispersion media that can be intravitally used and can make an active ingredient or a physiologically acceptable salt thereof suspended therein, which may be composed of one ingredient or may be a mixture of plural ingredients. It includes, for example, water, and water containing a solvent like an oil such as castor oil, soybean oil, and liquid paraffin. In the aqueous dispersion media used herein, 90 wt % or more of the whole solvent used as the dispersion media is water, which is preferably an aqueous solvent containing 95 wt % or more water, more preferably an aqueous solvent containing 99 wt % or more. Particularly preferably, the solvent used as the dispersion media is water. The dispersion media may comprise an additive such as a dispersant, a surfactant, an excipient, a tonicity agent, a buffer agent, a preservative, a wetting agent, and a pH adjuster which a skilled person well knows, in an amount that the additive cannot affect the stability and particle size of the active ingredient. In addition, the dispersion media may comprise an oil, an organic solvent such as ethanol, etc., in an amount that it cannot affect the stability and particle size of the active ingredient. In the suspension pharmaceutical composition to which a dispersion media is added, an active ingredient may exist in dispersed, emulsified, or enclosed state, and also the composition may be an emulsion.

The pH of the aqueous dispersion media should not be limited to a specific pH as long as it cannot affect the stability and particle size of the active ingredient, but which is generally 3-9, preferably 4-8, more preferably 5-8, particularly preferably 5-7.4. The pH of the dispersion medium can be adjusted with a pH adjuster mentioned below.

The pharmaceutical composition of the present invention may be provided after sterilization, wherein the sterilization can be done by, for example, filtrating, radiating, or autoclave-treating a suspension of suspension composition of the present invention. For example, the suspension composition in which the present solid composition is dispersed in the above-mentioned dispersion media, or the suspension composition as the process intermediate which is prepared in the above-mentioned process may be sterilized. Or, the solid composition as a lyophilized product may be sterilized by radiation. Or, the solid composition comprising an active ingredient, and the dispersion medium may be separately sterilized. And, the whole processes to prepare the present formulation or a part of the processes may be also done in a sterile environment.

The present pharmaceutical composition which is a liquid can be obtained by suspending the present solid composition in a dispersion media beforehand or before use, which may comprise an additive such as an excipient. The additive used herein may be added beforehand to the un-dried suspension composition which is a process intermediate of the solid composition, or may be added to the above-mentioned dispersion media. The excipient used in the present suspension formulation should not be limited, which includes a pharmaceutically acceptable excipient, for example, D-mannitol, lactose, trehalose, sorbitol, sucrose, glucose, α-cyclodextrin, β-cyclodextrin, γ-cyclodextrin, HP-β-cyclodextrin, and sulfobutylether-β-cyclodextrin. Two or more excipients, preferably 2-3 excipients may be used. The preferred example thereof may be D-mannitol, lactose, or trehalose.

The content of excipient is 0.1 parts or more by weight, more preferably 0.5 parts or more by weight, even more preferably 0.5-10 parts by weight, per 1 part by weight of the active ingredient, but not limited thereto. And, in the present suspension composition comprising the (D) ingredient, it is 1 mg/mL or more, preferably 5 mg/mL or more, and 1 mg/mL or more, preferably 5 mg/mL or more in a dispersion media.

The pharmaceutical composition of the present invention may comprise a dispersant for increasing the viscosity. The dispersant used herein includes, for example, carboxy vinyl polymer, polyvinylpyrrolidone (povidone), methylcellulose, hydroxypropylmethylcellulose (hypromellose), hydroxyethyl cellulose, hydroxypropylcellulose, polyvinyl alcohol, carboxymethylcellulose sodium (carmellose sodium), tyloxapol, gum ghatti, gum arabic, powdered acacia, karaya gum, xanthane gum, aminoalkyl methacrylate copolymer RS, propylene glycol alginate, sodium carboxymethyl starch, powdered agar, dioctyl sodium sulfosuccinate, and dextrin. And, two or more dispersants may be used.

The content of the dispersant should not be limited to a specific one, but which is 0.5 mg/mL-50 mg/mL, preferably 1 mg/mL-50 mg/mL, more preferably 5 mg/mL-50 mg/mL in the present suspension composition comprising the (D) ingredient, and 1 mg/mL or more, preferably 5 mg/mL or more, more preferably 10 mg/mL or more in the dispersion media.

The pharmaceutical composition of the present invention may comprise one or more of a tonicity agent, a buffer agent, a preservative, a wetting agent, or a pH adjuster.

The tonicity agent includes sodium chloride, potassium chloride, sorbitol, glucose, sucrose, D-mannitol, ethanol, oleic acid, magnesium silicate, light anhydrous silicic acid, and choline phosphate, preferably D-mannitol and sodium chloride.

The buffer agent includes sodium phosphate, disodium hydrogen phosphate, sodium dihydrogenphosphate, sodium acetate, citric acid, sodium citrate, sodium bicarbonate, and trometamol, preferably disodium hydrogen phosphate and citric acid.

The preservative includes a quaternary ammonium salt such as benzalkonium chloride, benzethonium chloride, and cetylpyridinium chloride; a p-oxybenzoate such as methyl p-hydroxybenzoate, ethyl p-hydroxybenzoate, propyl p-hydroxybenzoate, and butyl p-hydroxybenzoate; benzyl alcohol; phenethyl alcohol; sorbic acid; and sorbate; chlorhexidine gluconate solution.

The wetting agent includes ethanol, oleic acid, magnesium silicate, light anhydrous silicic acid, and choline phosphate.

The pH adjuster includes hydrochloric acid, citric acid, glacial acetic acid, phosphoric acid, boric acid, sodium dihydrogenphosphate, sodium hydroxide, potassium hydroxide, sodium carbonate, sodium bicarbonate, and dibasic sodium phosphate hydrate.

The suspension pharmaceutical composition of the present invention can be prepared with an active ingredient, in which the amount of the active ingredient is generally 1-200 mg, preferably 5-150 mg, more preferably 10-100 mg, particularly preferably 10-50 mg, per 1 mL of a dispersion medium, but the present invention should not be limited to the above-mentioned amounts.

The pH of the present suspension formulation is generally 3-9, preferably 3-8, more preferably 3-7.4. The pH of the suspension can be adjusted with the above-mentioned pH adjuster. For a suspension formulation comprising an acidic active ingredient, the concentration of the active ingredient in a suspension state can be made to be high by lowering the pH of the suspension to lower the solubility of the active ingredient particle in the suspension. On the contrary, for a suspension formulation comprising a basic active ingredient, the concentration of the active ingredient in a suspension state can be made to be high by raising the pH of the suspension to lower the solubility of the active ingredient particle in the suspension.

When the present pharmaceutical composition comprises an additive such as an excipient, a dispersant, a surfactant, an excipient, a tonicity agent, a buffer agent, a preservative, a wetting agent, and a pH adjuster, the additive(s) may be added beforehand to the suspension composition which is prepared in the process, or may be added to the prepared solid composition or the dispersion media to be added to the solid composition.

The osmotic pressure of the suspension pharmaceutical composition of the present invention is generally 20-1000 mOsm, preferably 100-700 mOsm, more preferably 180-500 mOsm, and particularly preferably 200-360 mOsm. The osmotic pressure of the suspension can be adjusted with the above-mentioned tonicity agent.

The above-mentioned osmotic pressure of the suspension pharmaceutical composition can be measured with the supernatant solution that is obtained, for example, by centrifuging the suspension. For example, an osmotic pressure measuring device "OSMOSTAT OM-6040" (ARKRAY, Inc.) can be used for the measurement.

The formulation of the present invention may comprise two or more active ingredients.

When the active ingredient is Compound A or a physiologically-acceptable salt thereof in the present invention, it is expected to have therapeutic effects for various ophthalmic diseases because the compound has an action inhibiting aldose reductase, and an action inhibiting VEGF production. Specifically, the present pharmaceutical composition comprising Compound A or a pharmaceutically acceptable salt thereof is useful as a agent for treating or preventing a disease particularly such as age-related macular degeneration, diabetic retinopathy, diabetic macular edema, macular edema, myopic choroidal neovascularization, retinal vein occlusion, choroidal neovascularization, uveitis, retinitis pigmentosa, proliferative vitreoretinopathy, and central serous chorioretinopathy, keratitis, conjunctivitis, neovascular glaucoma, dry eye, and cataract.

The dosage and administration of the ophthalmic suspension formulation comprising Compound A or a pharmaceutically acceptable salt thereof should be suitably defined based on the drug efficacy, administration route, symptom, age, body weight, etc. Preferred dosage and administration in the present invention is, for example, administering a suspension formulation comprising 1-500 mg/mL Compound A or a physiologically-acceptable salt thereof in eyedrops, in the amount of 1-2 drops every time for each eye, totally once to about 6 times a day. In general, the amount of one drop in eyedrops is 20-80 µL, preferably 30-50 µL. The administration period in the present invention should be decided depending on the symptom severity or the like, including, for example, one or more weeks, preferably about 1 week-about 4 weeks, and more preferably about 4 or more weeks.

EXAMPLES

In the following, the present invention is explained in detail by referring to Examples, Comparative examples, Tests, etc., but should not be limited thereto.

The measurements of mean particle sizes and D90 particle sizes in the present invention were carried out as shown below, considering the particle state, the scale of particle size, the solubility of the active ingredient, etc.

In order to measure the particle size of a solid active ingredient dispersed in a suspension, wherein the particle size is 1 nm-5 µm, preferably 10 nm-5 µm; the suspension is diluted with 50 or 100 parts of 0.01 mmol/L hydrochloric acid or 0.01 mmol/L sodium hydroxide solution, and the deluted sample is measured three times with an instrument, Zetasizer Nano S (Malvern Instruments Ltd.). The particle size distribution is measured by dynamic light scattering method, and the mean particle size and D90 particle size are calculated with material RI of 1.5, dispersant RI of 1.33, and sample viscosity of 0.9. The calculated mean particle size and D90 particle size were shown as the measured results.

For a big particle having a size of 5 µm or more which developed caused by crystal growth or aggregation, it is difficult to detect the particle. For such a big particle, it was evaluated with an optical microscope. The conditions for the observation are shown below, but are not limited thereto.

5 µL of a sample suspension is dropped on a slide glass, covered with a cover glass, and then analyzed with Manual System Microscope BX51 (OLYMPUS CORPORATION), wherein the shape of the active ingredient in the suspension is observed at 200-fold or 400-fold magnification.

For a nano-sized fine particle, it is difficult to analyze the shape of a fine particle precisely by the above-mentioned method. For such a nano-sized fine particle, it was evaluated with an electronic microscope as follows.

The concentration of each ingredient in a sample suspension is lowered by diluting it with water or dialysis membrane, the diluted sample is dropped on a test stage, and the solvent is evaporated to prepare a test sample. The test sample is analyzed with a scanning electron microscope S-3400N (Hitachi High-Technologies Corporation) or a transmission electron microscope JEM-2100HR (JEOL).

Examples 1-6, Comparative Examples 1-2: Preparation of Suspension (1)

Compound A and/or poloxamer 196/67 whose amounts are indicated in Table 1 were dissolved in 1,1-dimethylethanol in a warm-water bath (hereinafter, referred to as Solution A). In the same way, EG-05, mannitol, and/or the surfactant were dissolved in water, and then the pH of the solution was adjusted to 4.7 with hydrochloric acid and/or sodium hydroxide (hereinafter, referred to as Solution B). To Solution A (10 mL) stirred at about 1600 rpm with a magnetic stirrer, Solution B (30 mL) was injected with a syringe, and the stirring was continued for about more 3 minutes to give a suspension.

In the Examples, Comparative examples, Tests, and Tables, the "poloxamer 196/67" is polyoxyethylene (196) polyoxypropylene (67) glycol comprising polyoxyethylene units in 70 wt % (BASF in Japan, Product name: Kolliphor P 407), the "EG-05" is polyvinyl alcohol having saponification rate of 86.5-89.0% (Nippon Synthetic Chemical Industry Co., Ltd., Product name: Gohsenol EG-05), the "PS80" is polysorbate 80 (Merck), and the "mannitol" is D-mannitol (Merck or ROCKETJAPAN).

TABLE 1

| | Composition of Solution A (mg/mL) | | | | | Composition of Solution B (mg/mL) | | |
| --- | --- | --- | --- | --- | --- | --- | --- | --- |
| | | | surfactant | EG-05 | mannitol | | surfactant | |
| Example | Compound A | type | Concentration | | | type | Concentration | |
| Example 1 | 15.6 | poloxamer 196/67 | 9.36 | 10 | 40 | PS80 | 0.535 |
| Example 2 | 15.6 | No | — | 10 | 40 | PS80 | 0.535 |
| Example 3 | 15.6 | poloxamer 196/67 | 9.36 | 10 | 40 | No | — |
| Example 4 | 15.6 | poloxamer 196/67 | 0.585 | 10 | 40 | poloxamer 196/67 | 0.75 |
| Example 5 | 15.6 | poloxamer 196/67 | 0.585 | 10 | 40 | No | — |
| Example 6 | 15.6 | poloxamer 196/67 | 0.156 | 10 | 40 | poloxamer 196/67 | 0.75 |
| Comparative example 1 | 15.6 | No | — | 10 | 40 | No | — |
| Comparative example 2 | 15.6 | poloxamer 196/67 | 0.156 | 10 | 40 | No | — |

Examples 7-9, Comparative Examples 3-15: Preparation of Lyophilized Product (1)

Compound A and poloxamer 200/70 whose amounts are indicated in Table 2 were dissolved in 1,1-dimethylethanol in a warm-water bath (hereinafter, referred to as Solution C). In the same way, the hydrophilic polymer and/or mannitol were dissolved in water, and then the pH of the solution was adjusted to 5 with hydrochloric acid and/or sodium hydroxide (hereinafter, referred to as Solution D). To Solution D (15 mL) stirred with a magnetic stirrer in an ice bath, Solution C (5 mL) was injected with a plastic syringe, and the stirring was continued for about more 20 minutes in an ice bath to give a suspension. Glass vials were filled with the suspension (3.6 mL per vial), frozen at −80° C., and then lyophilized for about 3 days in a shelf-type lyophilizer (ULVAC Inc., the lyophilizer was also used in other Examples, and Comparative examples).

In the Examples, Comparative examples, Tests, and Tables, the "poloxamer 200/70" is polyoxyethylene (200) polyoxypropylene (70) glycol comprising polyoxyethylene units in 70 wt % (NOF CORPORATION, Product name: Unilube 70DP-950B), the "HPMC" is hydroxypropyl methylcellulose (Shin-Etsu Chemical Co., Ltd., Product name: TC-5R), the "HPC-L" is hydroxypropylcellulose (NIPPON SODA CO., LTD.), the "PVP" is polyvinylpyrrolidone (BASF in Japan, Product name: Kollidon 30), the "PEG400" is polyethyleneglycol 400 (nacalai tesque), the "PEG4000" is polyethyleneglycol 4000 (nacalai tesque), the "CMC-Na" is carboxymethylcellulose sodium (DKS Co., Ltd., Product name: Serogen), the "CVP" is carboxy vinyl polymer (Wako Pure Chemical, Product name: HIVISWAKO 104), and the "NH-17Q" is polyvinyl alcohol having saponification rate of 99.7% (Nippon Synthetic Chemical Industry Co., Ltd., Product name: Gohsenol NH-17Q).

TABLE 2

| Example | Composition of Solution C (mg/mL) | | Composition of Solution D (mg/mL) | | |
|---|---|---|---|---|---|
| | Compound A | poloxamer 200/70 | mannitol | hydrophilic polymer type | Concentration |
| Comparative example 3 | 15.6 | 2.34 | 13.3 | No | — |
| Comparative example 4 | 15.6 | 2.34 | 13.3 | EG-05 | 1.1 |
| Example 7 | 15.6 | 2.34 | 13.3 | EG-05 | 3.3 |
| Example 8 | 15.6 | 2.34 | 13.3 | EG-05 | 10 |
| Example 9 | 15.6 | 2.34 | 13.3 | EG-05 | 15 |
| Comparative example 5 | 15.6 | 2.34 | 13.3 | HPMC | 3.3 |
| Comparative example 6 | 15.6 | 2.34 | 13.3 | HPMC | 10 |
| Comparative example 7 | 15.6 | 2.34 | 13.3 | HPC-L | 10 |
| Comparative example 8 | 15.6 | 2.34 | 13.3 | PVP | 3.3 |
| Comparative example 9 | 15.6 | 2.34 | 13.3 | PVP | 10 |
| Comparative example 10 | 15.6 | 2.34 | 13.3 | PEG400 | 10 |
| Comparative example 11 | 15.6 | 2.34 | 13.3 | PEG4000 | 10 |
| Comparative example 12 | 15.6 | 2.34 | 13.3 | CMC-Na | 10 |
| Comparative example 13 | 15.6 | 2.34 | 13.3 | CVP | 1.1 |
| Comparative example 14 | 15.6 | 2.34 | 13.3 | NH-17Q | 10 |
| Comparative example 15 | 15.6 | 2.34 | 13.3 | NH-17Q | 2.5 |

Examples 10-26, Comparative Examples 16-22: Preparation of Lyophilized Product (2)

Compound A and/or the surfactant whose amounts are indicated in Tables 3 and 4 were dissolved in 1,1-dimethylethanol in a warm-water bath (hereinafter, referred to as Solution E). In the same way, EG-05, mannitol and/or the surfactant were dissolved in water, and then the pH of the solution was adjusted to 5 with hydrochloric acid and/or sodium hydroxide (hereinafter, referred to as Solution F). To Solution F (15 mL) stirred with a magnetic stirrer in an ice bath, Solution E (5 mL) was injected with a plastic syringe, and the stirring was continued for about more 20 minutes in an ice bath to give a suspension. Glass vials were filled with the suspension (3.6 mL per vial), frozen at −80° C., and then lyophilized for about 3 days in a shelf-type lyophilizer.

In the Examples, Comparative examples, Tests, and Tables, the "HCO-60" is polyoxyethylene hydrogenated castor oil 60 (Nikko Chemicals Co., Ltd.), the "HCO-20" is polyoxyethylene hydrogenated castor oil 20 (Nikko Chemicals Co., Ltd.), the "HCO-10" is polyoxyethylene hydrogenated castor oil 10 (Nikko Chemicals Co., Ltd.), the "HCO-5" is polyoxyethylene hydrogenated castor oil 5 (Nikko Chemicals Co., Ltd.), the "CO-3" is polyoxyethylene castor oil (Nikko Chemicals Co., Ltd.), the "SO-10V" is sorbitan monooleate (Nikko Chemicals Co., Ltd.), the "SO-15MV" is sorbitan sesquioleate (Nikko Chemicals Co., Ltd.), the "GO-991" is glyceryl monooleate (NOF CORPORATION), the "MYS-40MV" is polyoxyl 40 stearate (Nikko Chemicals Co., Ltd.), the "PS20" is polysorbate 20 (nacalai tesque), the "SOLUPLUS" is polyvinylcaprolactam-polyvinyl acetate-polyethylene glycol graft polymer (BASF in Japan), the "LL-810" is polyvinyl alcohol having saponification rate of 45.0-51.0% (Nippon Synthetic Chemical Industry Co., Ltd., Product name: GOHSENX LL-810), the "DPPC" is dipalmitoylphosphatidylcholine (NOF CORPORATION, Product name: COATSOME MC6060), the "SDS" is sodium lauryl sulfate (nacalai tesque), and the "Na deoxycholate" is sodium deoxycholate (nacalai tesque).

TABLE 3

| Example | Composition of Solution E (mg/mL) | | | Composition of Solution F (mg/mL) | | | |
|---|---|---|---|---|---|---|---|
| | Compound A | surfactant type | Concentration | mannitol | EG-05 | surfactant type | Concentration |
| Example 10 | 15.6 | HCO-60 | 2.34 | 13.3 | 10 | No | — |
| Example 11 | 15.6 | HCO-60 | 2.34 | 13.3 | 10 | No | — |

TABLE 3-continued

| | Composition of Solution E (mg/mL) | | | Composition of Solution F (mg/mL) | | | |
|---|---|---|---|---|---|---|---|
| | | surfactant | | | EG- | surfactant | |
| Example | Compound A | type | Concentration | mannitol | 05 | type | Concentration |
| Example 12 | 15.6 | HCO-20 | 1.17 | 13.3 | 10 | No | — |
| Example 13 | 15.6 | HCO-10 | 1.17 | 13.3 | 10 | No | — |
| Example 14 | 15.6 | HCO-5 | 1.17 | 13.3 | 10 | No | — |
| Example 15 | 15.6 | CO-3 | 1.17 | 13.3 | 10 | No | — |
| Example 16 | 15.6 | SO-10V | 1.17 | 13.3 | 10 | No | — |
| Example 17 | 15.6 | SO-15MV | 1.17 | 13.3 | 10 | No | — |
| Example 18 | 15.6 | GO-991 | 1.17 | 13.3 | 10 | No | — |
| Example 19 | 15.6 | MYS-40MV | 1.17 | 13.3 | 10 | No | — |
| Example 20 | 15.6 | MYS-40MV | 2.34 | 13.3 | 10 | No | — |
| Example 21 | 15.6 | PS80 | 1.17 | 13.3 | 10 | No | — |
| Example 22 | 15.6 | PS80 | 2.34 | 13.3 | 10 | No | — |
| Example 23 | 15.6 | PS20 | 1.17 | 13.3 | 10 | No | — |
| Example 24 | 15.6 | SOLUPLUS | 1.17 | 13.3 | 10 | No | — |
| Example 25 | 15.6 | LL-810 | 1.17 | 13.3 | 10 | No | — |
| Example 26 | 15.6 | poloxamer 200/70 | 1.17 | 13.3 | 10 | No | — |

TABLE 4

| | Composition of Solution E (mg/mL) | | | Composition of Solution F (mg/mL) | | | |
|---|---|---|---|---|---|---|---|
| | | surfactant | | | EG- | surfactant | |
| Example | Compound A | type | Concentration | mannitol | 05 | type | Concentration |
| Comparative example 16 | 15.6 | No | — | 13.3 | 10 | No | — |
| Comparative example 17 | 15.6 | PEG400 | 1.17 | 13.3 | 10 | No | — |
| Comparative example 18 | 15.6 | stearic acid | 1.17 | 13.3 | 10 | No | — |
| Comparative example 19 | 15.6 | DPPC | 1.17 | 13.3 | 10 | No | — |
| Comparative example 20 | 15.6 | No | — | 13.3 | 10 | SDS | 0.3 |
| Comparative example 21 | 15.6 | No | — | 13.3 | 10 | benzalkonium chloride | 0.3 |
| Comparative example 22 | 15.6 | No | — | 13.3 | 10 | Na deoxycholate | 0.3 |

Examples 27-42: Preparation of Lyophilized Product (3)

Compound A and the surfactant whose amounts are indicated in Table 5 were dissolved in 1,1-dimethylethanol in a warm-water bath (hereinafter, referred to as Solution G). In the same way, EG-05 and mannitol were dissolved in water, and then the pH of the solution was adjusted to 5 with hydrochloric acid and/or sodium hydroxide (hereinafter, referred to as Solution H). To Solution H (15 mL) stirred with a magnetic stirrer in an ice bath, Solution G (5 mL) was injected with a plastic syringe, and the stirring was continued for about more 20 minutes in an ice bath to give a suspension. Glass vials were filled with the suspension (3.6 mL per vial) (2 mL for Example 29 and Example 31), frozen at −80° C., and then lyophilized for about 3 days in a shelf-type lyophilizer.

In the Examples, Comparative examples, Tests, and Tables, the "poloxamer 240/60" is polyoxyethylene (240) polyoxypropylene (60) glycol comprising polyoxyethylene units in 75 wt % (NOF CORPORATION, Product name: Unilube 70DE-2620R), the "poloxamer 160/30" is polyoxyethylene (160) polyoxypropylene (30) glycol comprising polyoxyethylene units in 80 wt % (NOF CORPORATION, Product name: PLONON #188P), the "poloxamer 20/20" is polyoxyethylene (20) polyoxypropylene (20) glycol comprising polyoxyethylene units in 40 wt % (NOF CORPORATION, Product name: PLONON #124P), and the "poloxamer 30/35" is polyoxyethylene (30) polyoxypropylene (35) glycol comprising polyoxyethylene units in 40 wt % (NOF CORPORATION, Product name: PLONON #204).

TABLE 5

| Example | Composition of Solution G (mg/mL) | | | Composition of Solution H (mg/mL) | |
|---|---|---|---|---|---|
| | Compound A | surfactant type | Concentration | mannitol | EG-05 |
| Example 27 | 15.6 | poloxamer 200/70 | 0.39 | 13.3 | 10 |
| Example 28 | 15.6 | poloxamer 200/70 | 0.78 | 13.3 | 10 |
| Example 29 | 15.6 | poloxamer 200/70 | 2.34 | 13.3 | 10 |
| Example 30 | 15.6 | poloxamer 200/70 | 5.46 | 13.3 | 10 |
| Example 31 | 15.6 | poloxamer 200/70 | 7.02 | 13.3 | 10 |
| Example 32 | 7.8 | poloxamer 200/70 | 1.17 | 13.3 | 10 |
| Example 33 | 31.2 | poloxamer 200/70 | 1.56 | 13.3 | 10 |
| Example 34 | 31.2 | poloxamer 200/70 | 4.68 | 13.3 | 10 |
| Example 35 | 31.2 | poloxamer 200/70 | 2.34 | 13.3 | 10 |
| Example 36 | 31.2 | poloxamer 200/70 | 3.12 | 13.3 | 10 |
| Example 37 | 15.6 | poloxamer 240/60 | 1.17 | 13.3 | 10 |
| Example 38 | 15.6 | poloxamer 240/60 | 2.34 | 13.3 | 10 |
| Example 39 | 15.6 | poloxamer 160/30 | 1.17 | 13.3 | 10 |
| Example 40 | 15.6 | poloxamer 20/20 | 1.17 | 13.3 | 10 |
| Example 41 | 15.6 | poloxamer 30/35 | 1.17 | 13.3 | 10 |
| Example 42 | 15.6 | poloxamer 30/35 | 2.34 | 13.3 | 10 |

Examples 43-68: Preparation of Lyophilized Product (4)

Compound A and/or poloxamer 200/70 whose amounts are indicated in Tables 6 and 7 were dissolved in 1,1-dimethylethanol in a warm-water bath (hereinafter, referred to as Solution I). In the same way, EG-05, the excipient, and surfactant were dissolved in water, and then the pH of the solution was adjusted to 5 with hydrochloric acid and/or sodium hydroxide (hereinafter, referred to as Solution J). To Solution J (15 mL) (30 mL for Examples 58-61) stirred with a magnetic stirrer in an ice bath, Solution I (5 mL) (10 mL for Examples 58-61) was injected with a plastic syringe, and the stirring was continued for about more 20 minutes in an ice bath to give a suspension. Glass vials were filled with the suspension (2 mL per vial) (1.6 mL for Examples 49-68), frozen at −80° C., and then lyophilized for about 3 days in a shelf-type lyophilizer.

In the Examples, Comparative examples, Tests, and Tables, the "MPC30000" is poly(2-methacryloyloxy phosphorylcholine)-poly(n-butyl methacrylate) having a molecular weight of about 30000 (NOF CORPORATION, Product name: PUREBRIGHT MB-37-50T), and the "MPC100000" is poly(2-methacryloyloxy phosphorylcholine)-poly(n-butyl methacrylate) having a molecular weight of about 100000 (NOF CORPORATION, Product name: PUREBRIGHT MB-37-100T).

TABLE 6

| | Composition of Solution I (mg/mL) | | Composition of Solution J (mg/mL) | | | | |
|---|---|---|---|---|---|---|---|
| | | poloxamer | excipient | | EG- | surfactant | |
| Example | Compound A | 200/70 | type | Concentration | 05 | type | Concentration |
| Example 43 | 15.6 | 2.34 | mannitol | 13.3 | 10 | MPC 30000 | 0.5 |
| Example 44 | 15.6 | 2.34 | mannitol | 13.3 | 10 | MPC 30000 | 1 |
| Example 45 | 15.6 | 2.34 | mannitol | 13.3 | 10 | MPC 30000 | 3 |
| Example 46 | 31.2 | 4.68 | mannitol | 13.3 | 10 | MPC 30000 | 6 |
| Example 47 | 31.2 | 4.68 | mannitol | 13.3 | 10 | MPC 30000 | 3 |
| Example 48 | 31.2 | 0 | mannitol | 13.3 | 10 | MPC 30000 | 3 |
| Example 49 | 31.2 | 1.56 | mannitol | 13.3 | 10 | MPC 30000 | 0 |
| Example 50 | 31.2 | 2.34 | mannitol | 13.3 | 10 | MPC 30000 | 0 |
| Example 51 | 31.2 | 3.12 | mannitol | 13.3 | 10 | MPC 30000 | 0 |
| Example 52 | 31.2 | 1.56 | mannitol | 13.3 | 10 | MPC 30000 | 2 |
| Example 53 | 31.2 | 2.34 | mannitol | 13.3 | 13 | MPC 30000 | 2 |

TABLE 7

| Example | Composition of Solution I (mg/mL) Compound A | poloxamor 200/70 | Composition of Solution J (mg/mL) excipient type | Concentration | EG-05 | surfactant type | Concentration |
|---|---|---|---|---|---|---|---|
| Example 54 | 31.2 | 3.12 | mannitol | 13.3 | 10 | MPC 30000 | 2 |
| Example 55 | 31.2 | 1.56 | mannitol | 13.3 | 10 | MPC 30000 | 4 |
| Example 56 | 31.2 | 2.34 | mannitol | 13.3 | 10 | MPC 30000 | 4 |
| Example 57 | 31.2 | 3.12 | mannitol | 13.3 | 10 | MPC 30000 | 4 |
| Example 58 | 31.2 | 2.34 | mannitol | 13.3 | 10 | MPC 100000 | 2 |
| Example 59 | 31.2 | 2.34 | mannitol | 13.3 | 10 | MPC 100000 | 4 |
| Example 60 | 31.2 | 3.12 | mannitol | 13.3 | 10 | MPC 100000 | 2 |
| Example 61 | 31.2 | 3.12 | mannitol | 13.3 | 10 | MPC 100000 | 4 |
| Example 62 | 31.2 | 3.12 | mannitol | 6 | 10 | MPC 30000 | 2 |
| Example 63 | 31.2 | 3.12 | mannitol | 20 | 10 | MPC 30000 | 2 |
| Example 64 | 31.2 | 3.12 | trehalose | 6 | 10 | MPC 30000 | 2 |
| Example 65 | 31.2 | 3.12 | lactose | 6 | 10 | MPC 30000 | 2 |
| Example 66 | 31.2 | 3.12 | mannitol | 13.3 | 6.6 | MPC 30000 | 4 |
| Example 67 | 31.2 | 3.12 | mannitol | 13.3 | 13 | MPC 30000 | 4 |
| Example 68 | 31.2 | 3.12 | mannitol | 13.3 | 16 | MPC 30000 | 4 |

Examples 69-75, Comparative Examples 23-27: Preparation of Lyophilized Product (5)

Compound A, poloxamer 200/70, and/or polyvinyl alcohol whose amounts are indicated in Table 8 were dissolved in 1,1-dimethylethanol in a warm-water bath (hereinafter, referred to as Solution K). In the same way, mannitol and/or polyvinyl alcohol were dissolved in water, and then the pH of the solution was adjusted to 5 with hydrochloric acid and/or sodium hydroxide (hereinafter, referred to as Solution L). To Solution L (15 mL) stirred with a magnetic stirrer in an ice bath, Solution K (5 mL) was injected with a plastic syringe, and the stirring was continued for about more 20 minutes in an ice bath to give a suspension. Glass vials were filled with the suspension (3.6 mL per vial), frozen at −80° C., and then lyophilized for about 3 days in a shelf-type lyophilizer.

In the Examples, Comparative examples, Tests, and Tables, the "PVA32000" is polyvinyl alcohol having a molecular weight of about 32000 (Merck, Product name: polyvinyl alcohol PVA4-88 EMPROVE PhEur, USP, JPE), the "PVA40000" is polyvinyl alcohol having a molecular weight of about 40000 (Merck, Product name: PVA 5-88 EMPROVE PhEur, USP, JPE), the "PVA64000" is polyvinyl alcohol having a molecular weight of about 64000 (Merck, Product name: PVA 8-88 EMPROVE PhEur, USP, JPE), the "PVA135000" is polyvinyl alcohol having a molecular weight of about 135000 (Merck, Product name: PVA 26-88 EMPROVE PhEur, USP, JPE), the "PVA163000" is polyvinyl alcohol having a molecular weight of about 163000 (Merck, Product name: PVA 40-88 EMPROVE PhEur, USP, JPE), the "LL-920" is polyvinyl alcohol having saponification rate of 30.0-38.0% (Nippon Synthetic Chemical Industry Co., Ltd., Product name: GOHSENX LL-920), and the "LL-940" is polyvinyl alcohol having saponification rate of 34.0-41.0% (Nippon Synthetic Chemical Industry Co., Ltd., Product name: GOHSENX LL-940).

TABLE 8

| Example | Composition of Solution K (mg/mL) | | | | | Composition of Solution L (mg/mL) | | |
|---|---|---|---|---|---|---|---|---|
| | Compound A | poloxamer 200/70 | polyvinyl alcohol type | Concentration | mannitol | polyvinyl alcohol type | Concentration | |
| Example 69 | 15.6 | 2.34 | No | — | 13.3 | PVA 32000 | 10 | |
| Example 70 | 15.6 | 2.34 | No | — | 13.3 | PVA 40000 | 10 | |
| Example 71 | 15.6 | 2.34 | No | — | 13.3 | PVA 64000 | 10 | |
| Example 72 | 15.6 | 2.34 | No | — | 13.3 | PVA 64000 | 5 | |
| Example 73 | 15.6 | 2.34 | No | — | 13.3 | PVA 135000 | 10 | |
| Example 74 | 15.6 | 2.34 | No | — | 13.3 | PVA 163000 | 10 | |
| Comparative example 23 | 15.6 | 2.34 | No | — | 13.3 | PVA 163000 | 1.25 | |
| Comparative example 24 | 15.6 | 2.34 | LL-810 | 38 | 13.3 | No | — | |
| Comparative example 25 | 15.6 | 2.34 | LL-810 | 10 | 13.3 | No | — | |
| Example 75 | 15.6 | 2.34 | LL-920 | 38 | 13.3 | No | — | |
| Comparative example 26 | 15.6 | 2.34 | LL-920 | 10 | 13.3 | No | — | |
| Comparative example 27 | 15.6 | 2.34 | LL-940 | 38 | 13.3 | No | — | |

Examples 76-79, Comparative Example 28: Preparation of Lyophilized Product (6)

Compound A and poloxamer 200/70 whose amounts are indicated in Table 9 were dissolved in 1,1-dimethylethanol in a warm-water bath (hereinafter, referred to as Solution M). In the same way, EG-05 and mannitol were dissolved in water, and then the pH of the solution was adjusted to 5 with hydrochloric acid and/or sodium hydroxide (hereinafter, referred to as Solution N). To Solution N stirred with a magnetic stirrer in an ice bath, Solution M was injected with a plastic syringe, in which both the amounts were adjusted to make the total volume 20 mL and make the mixing volume ratio as defined in Table 9. And, the stirring was continued for about 20 minutes in an ice bath to give a suspension. Glass vials were filled with the suspension (1.6 mL per vial), frozen at −43° C., and then lyophilized for about 3 days in a shelf-type lyophilizer.

TABLE 9

| Example | Composition of Solution M (mg/mL) | | Composition of Solution N (mg/mL) | | Mixing volume ratio Solution M/ Solution N |
|---|---|---|---|---|---|
| | Compound A | poloxamer 200/70 | EG-05 | mannitol | |
| Example 76 | 31.2 | 2.34 | 10 | 13.3 | 2.5/7.5 |
| Example 77 | 31.2 | 2.34 | 12 | 15.6 | 3/7 |
| Example 78 | 31.2 | 2.34 | 14 | 18.6 | 3.5/6.5 |
| Example 79 | 31.2 | 2.34 | 10 | 13.3 | 3.5/6.5 |
| Comparative example 28 | 31.2 | 2.34 | 16 | 21.3 | 4/6 |

Examples 80-86: Preparation of Suspension (2)

The active ingredient and poloxamer 200/70 whose amounts are indicated in Table 10 were dissolved in ethanol or 1,1-dimethylethanol in a warm-water bath (hereinafter, referred to as Solution O). In the same way, EG-05 and mannitol were dissolved in water, and then the pH of the solution was adjusted to 5 (Examples 80-84) or 7.4 (Examples 85-86) with hydrochloric acid and/or sodium hydroxide (hereinafter, referred to as Solution P). To Solution P stirred with a magnetic stirrer in an ice bath, Solution O was injected with a plastic syringe, in which both the amounts were adjusted to make the total volume 20 mL and make the mixing volume ratio as defined in Table 10. And, the stirring was continued for about 20 minutes in an ice bath to give a suspension.

TABLE 10

| Example | Composition of Solution O (mg/mL) active ingredient type | Concentration | poloxamer 200/70 | solvent | Composition of Solution P (mg/mL) EG-05 | mannitol | Mixing volume ratio Solution O/Solution P |
|---|---|---|---|---|---|---|---|
| Example 80 | indomethacin | 79 | 5.925 | ethanol | 10 | 13.3 | 2.5/7.5 |
| Example 81 | indomethacin | 79 | 5.925 | ethanol | 10 | 13.3 | 1/9 |
| Example 82 | indomethacin | 31.6 | 2.34 | ethanol | 10 | 13.3 | 2.5/7.5 |
| Example 83 | indomethacin | 78 | 5.85 | 1,1-di-methylethanol | 10 | 13.3 | 1/9 |
| Example 84 | indomethacin | 31.2 | 2.34 | 1,1-di-methylethanol | 10 | 13.3 | 1/9 |
| Example 85 | blonanserin | 31.2 | 2.34 | 1,1-di-methylethanol | 10 | 13.3 | 1/9 |
| Example 86 | blonanserin | 31.2 | 1.17 | 1,1-di-methylethanol | 10 | 13.3 | 1/9 |

Examples 87-88: Preparation of Lyophilized Product (7)

Compound A (31.2 mg/mL) and poloxamer 200/70 (3.12 mg/mL) were dissolved in 1,1-dimethylethanol in a warm-water bath, in which each concentration was adjusted as shown in the brankets (hereinafter, referred to as Solution Q). In the same way, EG-05 (10 mg/mL), mannitol (13.3 mg/mL), and MPC 30000 (2 mg/mL) were dissolved in water, in which each concentration was adjusted as shown in the brankets, and then the pH of the solution was adjusted to 5 with hydrochloric acid and/or sodium hydroxide (hereinafter, referred to as Solution R). To Solution R (150 mL) stirred with a magnetic stirrer in an ice bath, Solution Q (50 mL) was added, and the stirring was continued in an ice bath to give a suspension. The mixing procedure was continued for 3 hours for Example 87, and for 6 hours for Example 88, and then the suspension (20 mL) was filtrated with Millex-GV (pore: 0.22 μm, material: PVDF). The pre-filtrated and post-filtrated suspensions were packed in different vials (4 mL per vial). The vials were frozen at −80° C., and then lyophilized for about 3 days in a shelf-type lyophilizer.

Example 89: Preparation of Suspension (3)

Compound A (31.2 mg/mL) and poloxamer 200/70 (3.12 mg/mL) were dissolved in 1,1-dimethylethanol in a warm-water bath, in which each concentration was adjusted as shown in the brankets (hereinafter, referred to as Solution S). In the same way, EG-05 (10 mg/mL) and mannitol (13.3 mg/mL) were dissolved in water, in which each concentration was adjusted as shown in the brankets, and then the pH of the solution was adjusted to 5 with hydrochloric acid and/or sodium hydroxide (hereinafter, referred to as Solution T). Solution S warmed in a warm-water bath (flow rate: 50 mL/min) and Solution T cooled at about 5° C. (flow rate: 150 mL/min) were sent to a forced thin film reactor (MTECHNIQUE, Product name: ULREA-SS11) in which the disk in the mixing part was rotated at 1700 rpm, and the suspension ejected out of the reactor was collected.

Test 1: Optical Microscopic Observation of Suspension (1)

Each 5 μL of the suspensions prepared in Examples 1-6 and Comparative examples 1-2 was dropped on a slide glass, covered with a 24 mm×32 mm cover glass, and observed with System Microscope BX51 (Olympus Corporation) at 200-fold or 400-fold magnification.

Test 2: Optical Microscopic Observation of Suspension (2)

To each lyophilized product prepared in Examples 7-9 and Comparative examples 3-15 was added 0.9 mL of water for injection, and each mixture was shaken with Vortex mixer to give each suspension. 5 μL of the suspension was dropped on a slide glass, covered with a 24 mm×32 mm cover glass, and observed with System Microscope BX51 (Olympus Corporation) at 200-fold or 400-fold magnification. In the same way, the pre-lyophilized suspensions were also observed.

The observations of shape in Test 1 were shown in FIGS. 1-8. According to FIGS. 1-8, it has been found that the crystal growth of Compound A can be inhibited and a fine particle of Compound A can be prepared, by using a surfactant in at least either one of 1,1-dimethylethanol or water.

The observations of shape in Test 2 were shown in FIGS. 9-40. According to FIGS. 9-40, it has been found that it is possible to prevent the aggregation of a fine particle of Compound A in a drying process and in a dried solid, by selecting polyvinyl alcohol out of hydrophilic polymers used generally as formula ingredients in a suspension and adding it to the suspension. In addition, the aggregation of the fine particle was not able to be prevented by adding completely-saponified polyvinyl alcohol (saponification rate: >99.7), thus it has been found that a partially-saponified form of polyvinyl alcohol (saponification rate: 99% or lower) specifically contributes to inhibit the aggregation of the fine particle.

Test 3: Measurement of Particle Size of Suspension (1)

The suspensions prepared in Examples 7-9 and Comparative example 4 (pre-lyophilization) were diluted 50-fold with 0.01 mmol/L hydrochloric acid, and then the particle size distribution of the suspensions was measured with Zetasizer Nano S. In addition, to each of the lyophilized products prepared in Examples 7-9 and Comparative example 4 was added 0.9 mL of water for injection, and each mixture was shaken with Vortex mixer to prepare suspensions. The suspensions were diluted 100-fold with 0.01 mmol/L hydrochloric acid, and then the particle size distribution of the suspensions was measured with Zetasizer Nano S.

Test 4: Stability Evaluation of Lyophilized Products (1)

The lyophilized products prepared in Examples 7-9 were stored under the circumstance of 40° C. for a week, and water for injection was added to the products in the same way as Test 3 to prepare suspensions. The suspensions were diluted 100-fold with 0.01 mmol/L hydrochloric acid, and then the particle size distribution of the suspensions was measured.

The measurement result of Test 3 is shown in Table 11 and the result of stability test in Test 4 is shown in Table 12. According to Table 11, it has been found that it is possible to prevent the growth of the particle size of the fine particle in a drying process and in a dried solid and to prepare a solid composition comprising a fine particle of Compound A having a mean particle size of 10-300 nm, by adding a partially-saponified form of polyvinyl alcohol whose content is 0.5 parts or more by weight per 1 part by weight of the active ingredient. In addition, according to Table 12, it has been found that a partially-saponified form of polyvinyl alcohol contributes to improve the stability of a fine particle in a solid composition and it is possible to prepare a solid composition which can make a fine particle of Compound A stably-retained, by adding a partially-saponified form of polyvinyl alcohol to the solid composition.

TABLE 11

| Example | Mean particle size (nm) | |
| --- | --- | --- |
| | Pre-lyophilization (cosolvent) | Post-lyophilization (water) |
| Comparative example 4 | 112 | 753 |
| Example 7 | 133 | 176 |
| Example 8 | 104 | 144 |
| Example 9 | 91 | 132 |

TABLE 12

| Example | Particle size distribution before storage test | | Particle size distribution after one-week storage at 40° C. | |
| --- | --- | --- | --- | --- |
| | Mean particle size (nm) | D90 particle size (nm) | Mean particle size (nm) | D90 particle size (nm) |
| Example 7 | 176 | 286 | 215 | 390 |
| Example 8 | 144 | 232 | 144 | 235 |
| Example 9 | 132 | 220 | 135 | 223 |

Test 5: Measurement of Particle Size of Suspension (2)

To each of the lyophilized products prepared in Examples 10-26 and Comparative examples 16-22 was added 0.9 mL of water for injection, and each mixture was shaken with Vortex mixer to prepare suspensions. The suspensions were diluted 100-fold with 0.01 mmol/L hydrochloric acid, and then the particle size distribution of the suspensions was measured with Zetasizer Nano S.

The measurement result of Test 5 is shown in Table 13. According to Table 13, it has been found that the particle of Compound A in each suspension can become a fine particle of having a mean particle size of 10-300 nm by adding a surfactant, in particular, a non-ionic surfactant to the suspension.

TABLE 13

| | particle size distribution | |
| --- | --- | --- |
| Example | mean particle size (nm) | D90 particle size (nm) |
| Example 10 | 104 | 155 |
| Example 11 | 121 | 189 |
| Example 12 | 129 | 192 |
| Example 13 | 147 | 224 |
| Example 14 | 161 | 246 |
| Example 15 | 162 | 251 |
| Example 16 | 177 | 254 |
| Example 17 | 178 | 272 |
| Example 18 | 188 | 278 |
| Example 19 | 174 | 259 |
| Example 20 | 184 | 268 |
| Example 21 | 144 | 210 |
| Example 22 | 161 | 241 |
| Example 23 | 178 | 258 |
| Example 24 | 124 | 188 |
| Example 25 | 125 | 196 |
| Example 26 | 71 | 104 |
| Comparative example 16 | 221 | 317 |
| Comparative example 17 | 233 | 344 |
| Comparative example 18 | 230 | 369 |
| Comparative example 19 | 224 | 320 |
| Comparative example 20 | 235 | 343 |
| Comparative example 21 | 242 | 339 |
| Comparative example 22 | 241 | 345 |

Test 6: Measurement of Particle Size of Suspension (3)

To each of the lyophilized products prepared in Examples 27-42 was added 0.9 mL of water for injection (0.5 mL for Example 29 and Example 31), and each mixture was shaken with Vortex mixer to prepare suspensions. The suspensions were diluted 100-fold with 0.01 mmol/L hydrochloric acid, and then the particle size distribution of the suspensions was measured with Zetasizer Nano S.

The measurement result of Test 6 is shown in Table 14. According to Table 14, it has been found that the particle of Compound A in each suspension can become a fine particle of having a mean particle size of 10-300 nm by adding polyoxyethylene polyoxypropylene glycol whose content is 0.02 to 0.3 parts by weight per 1 part by weight of the active ingredient, to the suspension. And, it has been also found that the particle of Compound A in each suspension can become a fine particle of having a mean particle size of 10-300 nm by adding polyoxyethylene polyoxypropylene glycol which comprises polyoxyethylene units in 40 to 80 wt %, to the suspension.

TABLE 14

| | Particle size distribution | |
| --- | --- | --- |
| Example | Mean particle size (nm) | D90 particle size (nm) |
| Example 27 | 184 | 353 |
| Example 28 | 74 | 109 |
| Example 29 | 157 | 241 |
| Example 30 | 206 | 356 |
| Example 31 | 237 | 506 |
| Example 32 | 169 | 287 |
| Example 33 | 113 | 186 |
| Example 34 | 155 | 243 |
| Example 35 | 99 | 163 |
| Example 36 | 102 | 161 |
| Example 37 | 113 | 177 |
| Example 38 | 147 | 215 |
| Example 39 | 140 | 210 |
| Example 40 | 200 | 285 |
| Example 41 | 114 | 174 |
| Example 42 | 165 | 233 |

Test 7: Stability Evaluation of Suspension

To the lyophilized products prepared in Examples 26, 27, 28, 39, 41, and 42 was added 0.9 mL of water for injection, and each mixture was shaken with Vortex mixer to prepare each suspension. Each suspension was stored under the circumstance of 25° C. for one day and for one week. The suspensions stored for each period were diluted 100-fold with 0.01 mmol/L hydrochloric acid, and then the particle size distribution of the suspensions was measured with Zetasizer Nano S.

The measurement result of Test 7 is shown in Table 15. According to Table 15, the particle size increased a little only in the suspension comprising a small amount of polyoxyethylene polyoxypropylene glycol. In many cases of the suspensions stored under the circumstance of 25° C., however, the particle size almost did not increase. Thus, it has been found that it is possible to prepare a liquid composition which can make a fine particle of Compound A stably-suspended, by adding polyoxyethylene polyoxypropylene glycol whose content is 0.02 to 0.3 parts by weight per 1 part by weight of the active ingredient, to the suspension.

TABLE 15

| Example | Mean particle size (nm) | | |
|---|---|---|---|
| | Before storage test | After one-day storage at 25° C. | After one-week storage at 25° C. |
| Example 26 | 71 | 73 | 74 |
| Example 27 | 184 | 217 | 210 |
| Example 28 | 74 | 76 | 76 |
| Example 39 | 140 | 142 | 142 |
| Example 41 | 114 | 112 | 113 |
| Example 42 | 165 | 166 | 166 |

Test 8: Measurement of Particle Size of Suspension (4)

To each of the lyophilized products prepared in Examples 43-68 was added 0.5 mL of water for injection (0.4 mL for Examples 49-68), and each mixture was shaken with Vortex mixer to prepare aqueous suspensions. The suspensions were diluted 100-fold with 0.01 mmol/L hydrochloric acid, and then the particle size distribution of the suspensions was measured with Zetasizer Nano S.

The measurement result of Test 8 is shown in Table 16. According to Table 16, it has been found that the fine particle of Compound A in each suspension can become much finer by adding MPC 30000 or MPC 100000, besides polyoxyethylene polyoxypropylene glycol, to the suspension. Further, it has been found that, by adding MPC polymer whose content is 0.05-0.6 parts by weight per 1 part by weight of the active ingredient to the suspension, it is possible to make Compound A a fine particle having a mean particle size of 10-300 nm, in more detail, a mean particle size of 150 nm or less; and it is possible to obtain a fine particle whose mean particle size is smaller by adding additional MPC polymer. And, it has been also found that the particle size distribution of the fine particle can be little affected by the content of EG-05, or the type and content of excipients.

TABLE 16

| | Particle size distribution | |
|---|---|---|
| Example | Mean particle size (nm) | D90 particle size (nm) |
| Example 43 | 138 | 230 |
| Example 44 | 123 | 201 |

TABLE 16-continued

| | Particle size distribution | |
|---|---|---|
| Example | Mean particle size (nm) | D90 particle size (nm) |
| Example 45 | 76 | 140 |
| Example 46 | 90 | 159 |
| Example 47 | 94 | 151 |
| Example 48 | 139 | 208 |
| Example 49 | 113 | 186 |
| Example 50 | 99 | 163 |
| Example 51 | 102 | 161 |
| Example 52 | 98 | 151 |
| Example 53 | 86 | 129 |
| Example 54 | 84 | 122 |
| Example 55 | 82 | 132 |
| Example 56 | 78 | 120 |
| Example 57 | 76 | 117 |
| Example 58 | 111 | 102 |
| Example 59 | 68 | 126 |
| Example 60 | 104 | 165 |
| Example 61 | 84 | 137 |
| Example 62 | 81 | 125 |
| Example 63 | 82 | 131 |
| Example 64 | 76 | 114 |
| Example 65 | 84 | 125 |
| Example 66 | 83 | 130 |
| Example 67 | 87 | 132 |
| Example 68 | 97 | 161 |

Test 9: Measurement of Particle Size of Suspension (5)

To each of the lyophilized products prepared in Examples 69-75 and Comparative examples 23-27 was added 0.9 mL of water for injection, and each mixture was shaken with Vortex mixer to prepare suspensions. The suspensions were diluted 100-fold with 0.01 mmol/L hydrochloric acid, and then the particle size distribution of the suspensions was measured with Zetasizer Nano S.

The measurement result of Test 9 is shown in Table 17. According to Table 17, it has been found that the particle of Compound A in each suspension can become a fine particle of having a mean particle size of 10-300 nm by adding polyvinyl alcohol having a saponification rate of 85-89% whose molecular weight is 150000 or less, to the suspension. And, it has been also found that the particle of Compound A in each suspension can become a fine particle of having a mean particle size of 10-300 nm by adding polyvinyl alcohol having a saponification rate of 30-55% to the suspension.

TABLE 17

| | Particle size distribution | |
|---|---|---|
| Example | Mean particle size (nm) | D90 particle size (nm) |
| Example 69 | 144 | 221 |
| Example 70 | 175 | 276 |
| Example 71 | 178 | 281 |
| Example 72 | 180 | 287 |
| Example 73 | 200 | 337 |
| Example 74 | 219 | 360 |
| Comparative example 23 | >5000 | >5000 |
| Comparative example 24 | 151 | 957 |
| Comparative example 25 | 571 | 965 |
| Example 75 | 162 | 294 |
| Comparative example 26 | 945 | 1230 |
| Comparative example 27 | 187 | 344 |

Test 10: Measurement of Particle Size of Suspension (6)

To each of the lyophilized products prepared in Examples 76-79 and Comparative example 28 was added 0.4 mL of water for injection, and each mixture was shaken with Vortex mixer to prepare suspensions. The suspensions were diluted 100-fold with 0.01 mmol/L hydrochloric acid, and then the particle size distribution of the suspensions was measured with Zetasizer Nano S.

The measurement result of Test 10 is shown in Table 18. According to Table 18, when the mixing ratio by volume (Solution M/Solution N) increases, the mean particle size correspondingly increases; and even when the mixing ratio by volume (Solution M/Solution N) increases to 4/6, the mean particle size of the prepared fine particle of the active ingredient is about 300 nm. It has been found that the present process can make an active ingredient a fine particle having a mean particle size of 10-300 nm, by adjusting the mixing ratio of a good solvent and a poor solvent.

TABLE 18

| | Particle size distribution | |
|---|---|---|
| Example | Mean particle size (nm) | D90 particle size (nm) |
| Example 76 | 95 | 157 |
| Example 77 | 126 | 189 |
| Example 78 | 184 | 269 |
| Example 79 | 189 | 283 |
| Comparative example 28 | 516 | 767 |

Test 11: Measurement of Particle Size of Suspension (7)

The suspensions prepared in Examples 80-86 were diluted 100-fold with 0.01 mmol/L hydrochloric acid (for Examples 80-84) or 0.01 mmol/L aqueous sodium hydroxide (for Examples 85-86), and then the particle size distribution of the suspensions was measured with Zetasizer Nano S.

The measurement result of Test 11 is shown in Table 19. According to Table 19, it has been found that the present process can make any active ingredients having various physicality a fine particle having a mean particle size of 10-300 nm.

TABLE 19

| | Particle size distribution | |
|---|---|---|
| Example | Mean particle size (nm) | D90 particle size (nm) |
| Example 80 | 162 | 245 |
| Example 81 | 143 | 220 |
| Example 82 | 102 | 149 |
| Example 83 | 179 | 318 |
| Example 84 | 77 | 117 |
| Example 85 | 288 | 431 |
| Example 86 | 245 | 338 |

Test 12: Determination of the Concentration of Compound A in Suspension

The pre-lyophilized suspensions prepared in Examples 87-88 (pre-filtrated and post-filtrated suspensions) were diluted with acetonitrile, and filtrated to remove additives which did not dissolve in acetonitrile. The filtrate was analyzed by reverse-phase high-performance liquid chromatography using C18 reverse-phase column (4.6 mm×150 mm, 5 μm), and a mobile phase composed of water, acetonitrile, tetrahydrofuran and perchloric acid (70%) to measure the concentration of Compound A. The spectroscopical detection of Compound A was performed with a wavelength of 220 nm.

Test 13: Measurement of Particle Size of Suspension (8)

To each of the lyophilized products prepared in Example 87 (pre-lyophilization and post-lyophilization) and Example 88 (only pre-lyophilization) was added 1 mL of water for injection, and each mixture was shaken with Vortex mixer to prepare aqueous suspensions. The suspensions were diluted 100-fold with 0.01 mmol/L hydrochloric acid, and then the particle size distribution of the suspensions was measured with Zetasizer Nano S.

The measurement result of Tests 12 and 13 is shown in Table 20. According to Table 20, it has been found that, the particle size distribution cannot greatly change after mixing Solution Q and Solution R, and then stirring the mixture in an ice bath for 6 hours, which means that the filtration of the suspension with a filter having a pore of 0.22 μm cannot lower the concentration of Compound A very much.

TABLE 20

| | Concentration of Compound A (mg/mL) | | Mean particle size (nm) | | D90 particle size (nm) | |
|---|---|---|---|---|---|---|
| Example | Pre-filtration | Post-filtration | Pre-filtration | Post-filtration | Pre-filtration | Post-filtration |
| Example 87 | 7.8 | 7.9 | 104 | 105 | 155 | 161 |
| Example 88 | 7.8 | 7.7 | 107 | No test | 161 | No test |

Test 14: Electron Microscopy of Fine Particle (1)

To the lyophilized product prepared in Comparative example 28 was added water for injection, and the mixture was shaken with Vortex mixer to prepare a suspension. The suspension was dialyzed in water for injection with a Fast SpinDIALYZER and a cellulose acetate membrane (HARVARD APPARATUS), and then the particle collected on the membrane was dried at room temperature. The dried membrane and particle were coated with platinum and observed with a scanning electron microscope S-3400N (Hitachi High-Technologies Corporation).

Test 15: Electron Microscopy of Fine Particle (2)

To a hydrophilic-treated collodion membrane was added dropwise 20 μL of the suspension prepared in Example 89. In addition, 20 μL of cold water (about 4° C.) was added dropwise thereto, and it was dried in vacuo at room temperature, and then observed with a transmission electron microscope JEM-2100HR (JEOL).

Figure 41:
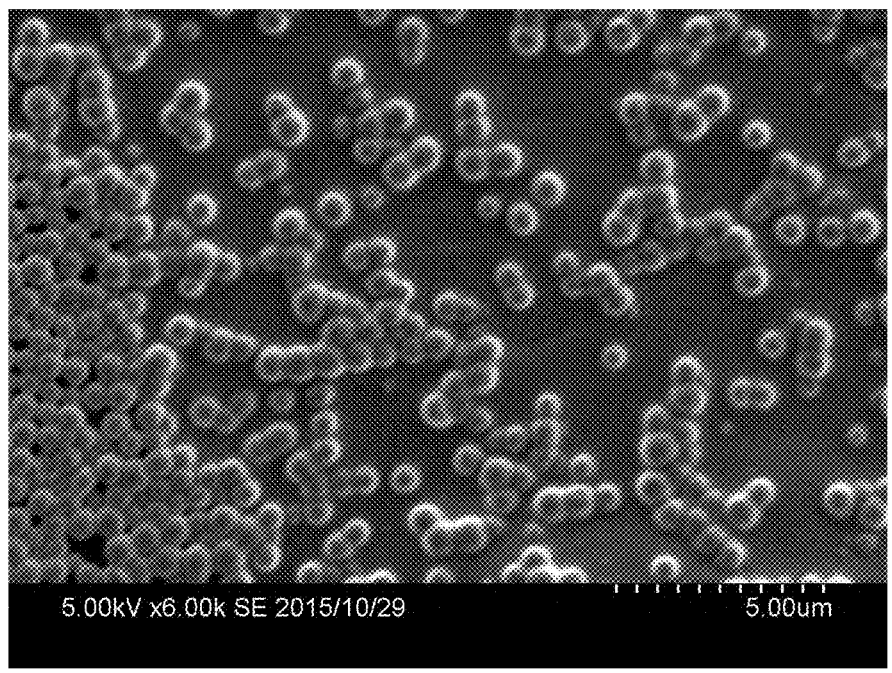
FIG. 41 shows a scanning electron microscopic image of the fine particle in the suspension of Comparative example 28.
Figure 42:
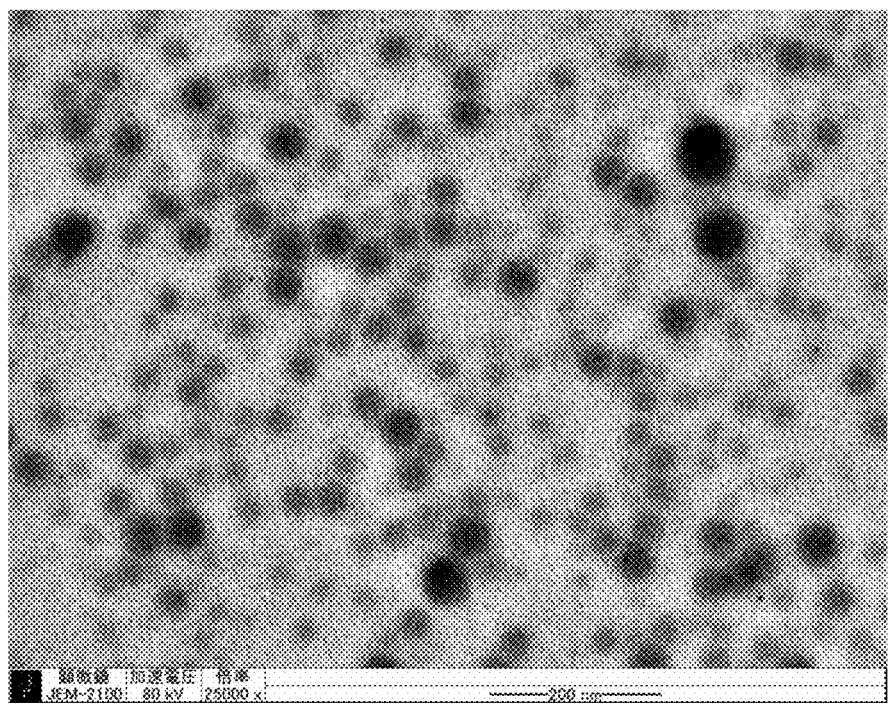
FIG. 42 shows a transmission electron microscopic image of the fine particle in the suspension of Example 89.

The results of the form observation in Tests 14 and 15 are shown in FIGS. 41 and 42, respectively. From the results in FIGS. 25 and 26, it has been found that the fine particle of an active ingredient prepared in the present process has spherical shape and high uniformity of the size.

Examples 90-92: Preparation of Lyophilized Product (8)

Compound A and poloxamer 200/70 whose amounts are indicated in Table 21 were dissolved in 1,1-dimethylethanol in a warm-water bath (hereinafter, referred to as Solution U). In the same way, EG-05, mannitol, and MPC 30000 were dissolved in water, and then the pH of the solution was adjusted to 5 with hydrochloric acid and/or sodium hydroxide (hereinafter referred to as Solution V). To Solution V stirred with a magnetic stirrer in an ice bath, Solution U was injected with a plastic syringe, in which both the amounts were adjusted to make the total volume 80 mL and make the mixing volume ratio as defined in Table 21. And, the stirring was continued for about 20 minutes in an ice bath to give a suspension. Glass vials were filled with the suspension (5 mL per vial), frozen at −80° C., and then lyophilized for about 3 days in a shelf-type lyophilizer.

TABLE 21

| Example | Composition of Solution U (mg/mL) | | Composition of Solution V (mg/mL) | | | Mixing volume ratio Solution U/ Solution V |
|---|---|---|---|---|---|---|
| | Compound A | poloxamer 200/70 | mannitol | EG-05 | MPC 30000 | |
| Example 90 | 40 | 4 | 10 | 12 | 5 | 1/4 |
| Example 91 | 40 | 4 | 10 | 12 | 2 | 1/4 |
| Example 92 | 40 | 4 | 10 | 12 | — | 1/4 |

Examples 93 and 94: Preparation of Lyophilized Product (9)

Compound A and poloxamer 200/70 whose amounts are indicated in Table 22 were dissolved in 1,1-dimethylethanol in a warm-water bath (hereinafter, referred to as Solution W). In the same way, EG-05, mannitol, MPC 30000 and boric acid were dissolved in water (hereinafter, referred to as Solution X). To Solution X stirred with a magnetic stirrer in an ice bath, Solution W was injected with a plastic syringe, in which both the amounts were adjusted to make the total volume 125 mL and make the mixing volume ratio as defined in Table 22. And, the stirring was continued for about more 20 minutes in an ice bath to give a suspension. Glass vials were filled with the suspension (5 mL per vial), frozen at −80° C., and then lyophilized for about 3 days in a shelf-type lyophilizer.

In the Examples, Tests, and Tables, the "boric acid" is boric acid (nacalai tesque).

TABLE 22

| Example | Composition of Solution W (mg/mL) | | Composition of Solution X (mg/mL) | | | | Mixing volume ratio Solution W/Solution X |
|---|---|---|---|---|---|---|---|
| | Compound A | poloxamer 200/70 | mannitol | EG-05 | MPC 30000 | boric acid | |
| Example 93 | 40 | 4 | 10 | 12 | 5 | 0.5 | 1/4 |
| Example 94 | 40 | 4 | 10 | 12 | 5 | 2 | 1/4 |

Test 16: Measurement of Particle Size of Suspension (9)

To each of the lyophilized products prepared in Examples 90-94 was added 0.8 mL of water for injection, and each mixture was shaken with Vortex mixer to prepare suspensions. The suspensions were diluted 100-fold with 0.01 mmol/L hydrochloric acid, and then the particle size distribution of the suspensions was measured with Zetasizer Nano S.

The measurement result of Test 16 is shown in Table 23. According to Table 23, it has been found that the particle of Compound A in each suspension can become a fine particle of having a mean particle size of 10-300 nm by adding Compound A, poloxamer 200/70, EG-05, mannitol, and MPC30000 to the suspension. And, it has been also found that the particle of Compound A in each suspension can become a fine particle of having a mean particle size of 10-300 nm by adding boric acid which is a pH adjuster used generally in eye drop to the suspension.

TABLE 23

| Example | Mean particle size (nm) |
|---|---|
| Example 90 | 85.2 |
| Example 91 | 95.7 |
| Example 92 | 103.7 |
| Example 93 | 93.3 |
| Example 94 | 90.1 |

Test 17: Stability Evaluation of Lyophilized Products (2)

The lyophilized products prepared in Examples 90-92 were stored under the circumstance of 25° C. for a month, and water for injection was added to the products to prepare suspensions. The suspensions were diluted 100-fold with 0.01 mmol/L hydrochloric acid, and then the particle size distribution of the suspensions was measured.

The result of stability test in Test 17 is shown in Table 24. According to Table 24, it has been found that the particle size in all the suspensions did not grow even when they were stored under the circumstance of 25° C. for a month and it is possible to prepare a solid composition which can make a fine particle of Compound A stably-retained, by adding Compound A, poloxamer 200/70, EG-05, mannitol, and MPC 30000 to the suspension.

TABLE 24

| Example | Particle size distribution before storage test Mean particle size (nm) | Particle size distribution after one-month storage at 25° C. Mean particle size (nm) |
|---|---|---|
| Example 90 | 85.2 | 80.7 |
| Example 91 | 95.7 | 91.4 |

TABLE 24-continued

| Example | Particle size distribution before storage test Mean particle size (nm) | Particle size distribution after one-month storage at 25° C. Mean particle size (nm) |
|---|---|---|
| Example 92 | 103.7 | 104.7 |

INDUSTRIAL APPLICABILITY

According these Examples, Comparative examples, Tests, and the like, by using the present composition and the process thereof, it is possible to provide a suspension composition and a solid composition which has a good stability to comprise an active ingredient as a fine particle having a mean particle size of 10-300 nm, preferably 10-200 nm.

The invention claimed is:

1. A composition, comprising:
   (R)-(-)-2-(4-bromo-2-fluorobenzyl)-1,2,3,4-tetrahydro-pyrrolo[1,2-a]pyrazine-4-spiro-3'-pyrrolidine-1,2',3,5'-tetraone or a pharmaceutically acceptable salt thereof as an active ingredient;
   a polyvinyl alcohol having a saponification rate of 55-99%; and
   a non-ionic surfactant,
   wherein the active ingredient has a mean particle size of 10-300 nm.

2. The composition of claim 1, wherein the active ingredient has a D90 particle size of 300 nm or less.

3. The composition of claim 1, wherein the mean particle size of the active ingredient is 10-200 nm.

4. The composition of claim 1, wherein the polyvinyl alcohol has a molecular weight of 150000 or less.

5. The composition of claim 1, wherein the non-ionic surfactant is at least one selected from the group consisting of polyoxyethylene polyoxypropylene glycol, polyoxyethylene hydrogenated castor oil, polyoxyethylene castor oil, polyoxyethylene sorbitan fatty acid ester, polyethylene glycol monostearate, sorbitan monooleate, sorbitan sesquioleate, glyceryl monooleate, and a polyvinyl alcohol having a saponification rate of less than 55%.

6. The composition of claim 5, wherein the non-ionic surfactant is polyoxyethylene polyoxypropylene glycol comprising at least one kind of polyoxyethylene units in 40 wt % or more.

7. The composition of claim 6, wherein the polyoxyethylene polyoxypropylene glycol is at least one selected from polyoxyethylene (160) polyoxypropylene (30) glycol, and polyoxyethylene (200) polyoxypropylene (70) glycol.

8. The composition of claim 1, wherein the content of the non-ionic surfactant is 0.02 to 0.8 parts by weight per 1 part of the active ingredient.

9. The composition of claim 1, further comprising:
   poly(2-methacryloyloxy phosphorylcholine)-poly(n-butyl methacrylate).

10. The composition of claim 9, wherein poly(2-methacryloyloxy phosphorylcholine)-poly(n-butyl methacrylate) is included at a content of 0.05 to 0.6 parts by weight per 1 part of the active ingredient.

11. The composition of claim 1, further comprising:
    a pharmaceutically acceptable excipient.

12. The composition of claim 11, wherein the excipient is at least one selected from the group consisting of mannitol, trehalose, and lactose.

13. The composition of claim 1, further comprising:
    an aqueous dispersion media.

14. The composition of claim 13, wherein the composition is dispersed in the aqueous dispersion media, and the active ingredient is in a suspension state.

15. The composition of claim 1, further comprising:
    a mixed solution which includes $C_{1-4}$ lower alcohol and water and has a water content of 50 vol % or more,
    wherein the active ingredient in the mixed solution is a manufacturing intermediate which is in a suspended state.

16. The composition of claim 15, wherein the water content of the mixed solution is 65 vol % or more.

17. The composition of claim 15, wherein the lower alcohol in the mixed solution is at least one selected from the group consisting of ethanol, 1-propanol, 2-propanol, 1,1-dimethylethanol, 1,2-ethanediol, 1,2-propanediol, 1,3-propanediol, and 1,2,3-propanetriol.

18. The composition of claim 17, wherein the lower alcohol in the mixed solution is ethanol or 1,1-dimethylethanol.

19. The composition of claim 15, wherein the active ingredient is included at a content of 1.5-20 mg/mL.

20. A solid composition, produced by a process including drying the composition of claim 15.

21. A process of producing the composition of claim 1, comprising:
    mixing Liquid 1 and Liquid 2,
    wherein Liquid 1 includes the active ingredient in a water-miscible $C_{1-4}$ organic solvent that may include 30 vol % or less water, Liquid 2 includes the polyvinyl alcohol having a saponification rate of 55-99%, and at least one of Liquid 1 and Liquid 2 includes the non-ionic surfactant.

22. The process of claim 21, wherein Liquid 1 comprises the non-ionic surfactant.

23. The process of claim 21, wherein Liquid 1 and Liquid 2 are mixed at a volume ratio of 0.5: 9.5-4: 6.

24. The process of claim 23, wherein the volume ratio of Liquid 1 and Liquid 2 is 0.5: 9.5-3.5: 6.5.

25. The process of claim 21, wherein the active ingredient is included in Liquid 1 and Liquid 2 at a total content of 1.5-20 mg/mL.

26. The process of claim 21, wherein the water-miscible $C_{1-4}$ organic solvent is at least one selected from the group consisting of a $C_{1-4}$ lower alcohol and acetone.

27. The process of claim 21, wherein the water-miscible $C_{1-4}$ organic solvent is a $C_{1-4}$ lower alcohol.

28. The process of claim 26, wherein the $C_{1-4}$ lower alcohol is at least one selected from the group consisting of ethanol, 1-propanol, 2-propanol, 1,1-dimethylethanol, 1,2-ethanediol, 1,2-propanediol, 1,3-propanediol, and 1,2,3-propanetriol.

29. The process of claim 28, wherein the lower alcohol is ethanol or 1,1-dimethylethanol.

30. The process of claim 21, wherein Liquid 1 comprises the non-ionic surfactant, and Liquid 2 further comprises poly(2-methacryloyloxy phosphorylcholine)-poly(n-butyl methacrylate).

31. The process of claim 21, wherein Liquid 1 comprises the non-ionic surfactant, and Liquid 2 further comprises a pharmaceutically acceptable excipient.

32. The process of claim 21, further comprising:
    filter-sterilizing a mixture of Liquid 1 and Liquid 2 after the mixing.

33. A process of producing a solid composition, comprising:
    drying in vacuo the composition of claim 1.

34. A process of producing a suspension, comprising:
    producing the solid composition by the process of claim 33; and
    suspending the solid composition in an aqueous dispersion media.

35. The process of claim 34, wherein the aqueous dispersion media is water.

36. The solid composition, produced by the process of claim 33.

37. A composition, comprising:
    the solid composition of claim 36; and
    an aqueous dispersion media.

38. The composition of claim 1, wherein the polyvinyl alcohol is included in an amount of 0.5 to 5 parts by weight per 1 part by weight of the active ingredient.

* * * * *